(12) United States Patent
Balas

(10) Patent No.: US 11,619,548 B2
(45) Date of Patent: Apr. 4, 2023

(54) HYBRID SPECTRAL IMAGING DEVICES, SYSTEMS AND METHODS

(71) Applicant: QCELL PC, Crete (GR)

(72) Inventor: Konstantinos Balas, Chania (GR)

(73) Assignee: QCELL PC, Chania (GR)

( * ) Notice: Subject to any disclaimer, the term of this patent is extended or adjusted under 35 U.S.C. 154(b) by 95 days.

(21) Appl. No.: 17/242,138

(22) Filed: Apr. 27, 2021

(65) Prior Publication Data
US 2021/0381893 A1 Dec. 9, 2021

Related U.S. Application Data

(63) Continuation-in-part of application No. 16/527,081, filed on Jul. 31, 2019, now Pat. No. 10,989,595.
(Continued)

(51) Int. Cl.
*G01N 33/02* (2006.01)
*G01J 3/28* (2006.01)
(Continued)

(52) U.S. Cl.
CPC .......... *G01J 3/2823* (2013.01); *G01N 33/02* (2013.01); *G01N 33/4833* (2013.01); *G01J 3/0264* (2013.01); *G01J 2003/2826* (2013.01)

(58) Field of Classification Search
CPC ............ G01N 33/025; G01J 2003/2826; G01J 3/2823
See application file for complete search history.

(56) References Cited

PUBLICATIONS

Xiaolin Bi, "Multihyperspectral Microscopic Imaging for the Precise Identification of Pollen", Jun. 25, 2018 (Year: 2018).*
(Continued)

*Primary Examiner* — Maurice C Smith
(74) *Attorney, Agent, or Firm* — DP IP Group; Franco De Liguori

(57) ABSTRACT

A hybrid spectral imager apparatus has an imaging head arrangement (IHA), a control and processing unit (CPU), and a display. The IHA includes an optical imager, multiband filtering optics (MBFO), and a sensor arrangement. The optical imager collects and focuses an image of a target scene or object along an imaging path. The multiband optics includes a beam divider for generating at least two replica images of the target image, and a multiband filter (MF) interposed into the imaging path and effecting multi-bandpass filtering in the image replicas. The sensor arrangement has at least one Mosaic filter array (MFA) focal plane array (FPA) sensor onto which the multiband filtered image replicas are focused, and a focal plane array masked, in a pixelized manner, with at least three wide-band primary color-type filters, with each primary color-type response separating and capturing one single-band. The CPU is coupled to the IHA and is configured to execute program instructions for calibrating image acquisition processes, controlling and synchronizing the acquisition/capturing of the image replicas by the MFA sensor arrangement, and spectrally purifying the MFA sensor arrangement responses to compensate band cross-talking between the MFA and the MF. The display is configured to display on a user interface at least the acquired single-band images. The CPU is further configured to reconstruct and display, on the display, a set of at least three different single-band images per MFA-FPA sensor employed. The IHA is configured to capture sets of different single-band images for video snapshot spectral imaging at desired spectral bands within the FPA sensor arrangement spectral sensitivity range.

26 Claims, 12 Drawing Sheets

Related U.S. Application Data

(60) Provisional application No. 62/713,019, filed on Aug. 1, 2018.

(51) Int. Cl.
  *G01N 33/483* (2006.01)
  *G01J 3/02* (2006.01)

(56) References Cited

PUBLICATIONS

Lizhi Wang, "Compressive Hyperspectral Imaging with Complementary RGB Measurements", 2016 IEEE (Year: 2016).*

* cited by examiner

HYBRID SPECTRAL IMAGING DEVICES, SYSTEMS AND METHODS

RELATED APPLICATIONS

This application is a continuation-in-part application and claims the benefit of U.S. Non-Provisional patent application Ser. No. 16/527,081, filed Jul. 31, 2019, now U.S. Pat. No. 10,989,595, issued Apr. 27, 2021, which claims the benefit of priority of U.S. Provisional Patent Application No. 62/713,019, filed on Aug. 1, 2018.

BACKGROUND

Technical Field

The present application generally relates to imaging. In particular, but not exclusively, the present application relates to hyperspectral imaging and to snapshot spectral imaging. More particularly, but not exclusively, the present application relates to use image splitting and filtering optics for miniaturized, video-snapshot spectral imaging and multiple snapshot hyperspectral imaging, combined with spectral estimation for achieving expanded color gamut spectral photography and for spectral and chemical mapping of natural, artificial and biological tissue objects.

Background Information

Hyperspectral imaging is widely used in numerus applications. Acquiring spectral information together with spatial information is a challenging technical problem with many solutions.

Among the most popular solutions are the ones based on either the spatial scanning of a scene with conventional point or line spectrometers or on the spectral scanning utilizing imaging monochromators, also known as staring spectral imagers. Spatial scanning hyperspectral imagers include, for example, push-broom, and whiskbroom spectral imagers. The staring category includes filters wheels, Acousto-optic Tunable Filters (AOTFs), Liquid Crystal Tunable Filters (LCTFs), Interferometric systems, Linear Variable Interference Filters (LVIF), tunable Fabry-Perot cavities, to name some. Tunable light sources, synchronized with a regular camera comprise a low-cost option for capturing spectral images in every wavelength-tuning step of the light source; however, they clearly comprise a suboptimal solution in remote sensing applications due to the random contributions of the ambient light. In general, scanning hyperspectral imagers suffer from the main drawback of requiring significant time to scan their full operation wavelength range, which makes them impractical when their intended use is the analysis of moving targets, or targets whose spectral characteristics are time dependent.

Snapshot (instant) spectral imagers have emerged as the solution to this problem. This category includes solutions relying on single-shot capturing of multiplexed spatial and spectral information, and the reconstruction of spectral images with post processing. Coded aperture and tomographic technologies belong to this class of instant spectral imagers.

The main deficiency of snapshot spectral imagers based on the multiplexing of spatial and spectral information is the trade-off between spatial and spectral resolution, often requiring relatively long post-processing time, something that it is practically prohibitive for video-rate spectral imaging. The real time aspect of spectral imaging is, for example, essential when spectral imaging triggers or guides actions in biomedical or industrial applications.

Pixelized spectral imagers offer real time snapshot spectral imaging and are constructed by replacing the three primary color filter arrays, used in color cameras, with a mosaic arrangement of multiple, spectrally non-overlapping bandpass filters. Typically, these filters have spectrally successive peak wavelengths between one to one another. Pixelized spectral imagers provide real-time display, at the cost, however, of the spatial resolution. In both multiplexed and pixelized spectral imagers, increase in spectral dimensionality is obtained at the cost of spatial resolution. Particularly, spatial resolutions of 300×300 pixels are typical, something unacceptable for a long list of applications, including professional photography, medical imaging and nondestructive testing. Recent publications describe methods integrating together pixelized spectral imagers with regular, 3-color-high resolution cameras with the purpose of virtually expanding the spatial information of the former. However, this requires significant post-processing time, which cancels the advantage of pixelized over multiplexing spectral imagers in terms of real time, simultaneous display of spectral images. More importantly, due to the very high heterogeneity of the spatial information of natural scenes, modeling and estimation of the missing spatial information is a time consuming, computationally intensive and error-prone procedure.

SUMMARY

The present invention aims to provide a hybrid spectral imager, mitigating the limitations present in prior art spectral imaging systems.

According to a first aspect of the present invention the disclosed hybrid spectral imager comprises:
an imaging head arrangement (IHA) comprising:
optical imaging means for collecting and focusing an image of a target scene or object along an imaging path;
multiband filtering optics (MBFO) means comprising:
beam divider means for generating at least two replica images of the target image;
tunable multiband filtering (TMF) means interposed into the imaging path and effecting a tunable multi-bandpass filtering in said images replicas;
a mosaic filter array (MFA) sensor arrangement comprising at least one MFA-focal plane array (FPA) sensor onto which said multiband filtered image replicas are focused, comprising focal plane array means masked, in a pixelized manner, with at least three wide-band primary color-type filters, with each primary color-type response separating and capturing one single-band image component from said multiband-filtered image replicas;
a control and processing unit (CPU) coupled to the imaging head arrangement, executing program instructions for: calibrating image acquisition processes; controlling and synchronizing the acquisition/capturing of the image replicas by the MFA sensor arrangement at given tuning step of the TMF and for a plurality of said tuning steps; spectrally purifying the MFA sensor arrangement responses to compensate band cross-talking between the MFA and the TMF;
display means for displaying on a user interface means at least the acquired single-band images;
wherein the CPU is configured to reconstruct and display, on said display means, a set of at least three different single-band images per MFA-FPA sensor employed;
wherein the CPU is configured to tune the TMF for selecting the center wavelengths of the sets of different single-band images for video snapshot spectral imaging at desired spectral bands and/or capturing a certain number of sets of different single-band images at a given tuning step and a plurality of sets in a multistep procedure, lasting until collecting a full hyperspectral cube data-set set comprising at least 30 single band images, within the FPA sensor's spectral sensitivity range.

According to embodiments of the first aspect, the CPU is configured to execute program instructions for identifying in a target scene-specific or object-specific spectral database, a set of critical spectral bands (CSB) corresponding to wavelengths populated with prominent spectral features. For example, said prominent spectral features correspond to peaks, and/or valleys, and/or slops of the captured spectra.

According to embodiments of the first aspect, the CPU is configured to execute program instructions for restoring a full spectrum from the MFA-sensor arrangement responses, captured at sparsely sampled data points along the spectrum, by fitting the responses captured at the sparsely sampled data points with a trained spectral estimation model and associated algorithms. According to embodiments of the first aspect, the sparsely sampled data-point correspond to the set of CSB.

According to embodiments of the first aspect, the CPU is configured for generating a spectral cube containing the set of snapshot spectral images captured by said MFA-sensor array means and one set of estimated spectral images, all together being displayed at video rates.

According to embodiments of the first aspect, said estimated spectral images are obtained from the estimated data points of said reconstructed spectra for all image pixels, as a two-dimensional array comprising intensity values corresponding to a specific wavelength band that belongs to the reconstructed portions of said spectra.

According to embodiments of the first aspect, the spectral estimation models and algorithms belong to a class of algorithms comprising, at least in apart, Least Squares, Wiener Estimation, Kernel Methods, Artificial Neural Networks, Sparse Reconstruction and Deep Learning approaches. For example, depending on the application, one or more of the models and algorithms in the group may be used to estimate the missing data points for the estimated spectral images.

According to embodiments of the first aspect, said CPU is configured to execute program instructions for spectral classification of a spectral imaging data set and for displaying a spectral thematic map of the spectral classification on the display means.

According to embodiments of the first aspect, said spectral classification utilizes a supervised classifier and a spectral data-set stored in a database with spectra having chemical identities and labels for converting the spectral thematic map to a chemical map or to a diagnostic map.

According to embodiments of the first aspect, the optical imaging means are selected from a group including photography lenses, microscopy optics, collimating optics infinity corrected optics rigid or flexible endoscopes, and telescopes. The optical imaging means is selected according to the application, or user requirements.

According to embodiments of the first aspect, said target scene or object is selected from a group at least in part human or animal tissue, plant tissue, landscape scene, processed or raw food material, natural material, manmade material, in aerial, land or underwater imaging conditions.

According to embodiments of the first aspect, the MBFO means comprise at least in part cube beam splitters, plate beam splitters, polarizing beam splitters, pentagon beam splitter/dividers, right angle prism with mirror coated legs, mirror coated pyramid prisms with mirror-coated legs, polka-dot beam splitters and pellicle beam splitters.

According to embodiments of the first aspect, said TMF comprise at least in part angle depending spectral transmittance filtering (ADSF) in the forms of, ADSF-type dichroic and polychroic mirrors, and ADSF-type multi-bandpass filters, spatial light modulators, acousto-optic, liquid crystal spectral modulators, surface plasmons filters and combinations thereof.

According to embodiments of the first aspect, said TMF is an ADSF-type multiband reflection and/or transmission filter, having the property of tuning at about 15% the bands' center wavelength, when it is tilted within an angle range of ±30°.

According to embodiments of the first aspect, said ADSF-type filter means is disposed onto a tiltable axis of a tilting actuator means, and wherein the tilting actuator is selected from a group including galvanic electromechanical elements, rotary actuators, motors, rotary solenoids, magnetic, electrical, thermal actuators and microelectromechanical system (M EMs). The implementation of the actuator depends on the desired application and may involve the use of one or more elements from the group, and/or other means known to the skilled person in the art.

According to embodiments of the first aspect, said CPU and display means comprise, at least in part, microcontroller units, memory units, Field Programmable Gate Arrays (FPGAs), mobile phones, tablet computers, lap top computers, flat displays and video googles. For example, the CPU and display means may be implemented in various ways, which may involve one or more of the elements mentioned in the group, and/or any other means known to the skilled person in the art.

According to embodiments of the first aspect, the beam divider is a tilting pentaprism beam divider, disposed onto said tiltable axis of a tilting actuator means, wherein said TMF is an ADSF-type polychroic mirror coating deposited onto the first reflection surface of said pentaprism beam divider reflecting and transmitting two multiband filtered image replicas, at tilting angle-invariant orthogonal directions, and wherein the IHA comprises two MFA-FPA sensor's disposed at the transmission/reflection focal planes of said optical imaging means for capturing the transmitted and reflected multiband filtered image replicas substantially simultaneously.

According to embodiments of the first aspect, the beam divider is a tilting pentaprism beam divider, disposed onto the tiltable axis of the tilting actuator means, wherein the TMF comprises a pair of ADSF-type multiband-pass filters disposed onto the pentaprism surfaces from which the image replicas are emerging, the ADSF-type filters transmitting two multiband filtered image replicas at tilting angle invariant orthogonal directions, and wherein the IHA comprises two MFA-FPA sensor's disposed at the transmission/reflection focal planes of said optical imaging means for capturing the transmitted multiband filtered image replicas substantially simultaneously.

According to embodiments of the first aspect, the first reflection surface of the pentaprism is cemented together with a triangle prism such that the pentaprism's rear surface is parallel with the front surface of the penda-prism to compensate for image distortion effects According to embodiments of the first aspect, the beam divider is a beam splitting element disposed at a fixed location in the imaging path, defined as the space between the rear ending of said optical imaging optics means and their focal plane, wherein the TMF comprises a pair of ADSF-type multiband-pass filters, each disposed onto the tiltable axis of two tilting actuator means, interposed into the split ray paths, and wherein the IHA comprises two MFA sensor arrangements for capturing the transmitted multiband filtered image replicas substantially simultaneously.

According to embodiments of the first aspect, the beam divider is a Köster prism-type beam divider configured so that the bisector of one of its angles is coated with an ADSF-type filter and wherein the IHA comprise a single MFA sensor arrangement, disposed onto the opposite side of the dissected angle, capturing two multiband image replicas into two different areas of said single MFA sensor.

According to embodiments of the first aspect, the beam divider comprises a multisided reflector with at least two sides being mirror-coated, the mirrored coated sides being configured for dividing the incoming light beam into at least two oppositely reflected components.

According to embodiments of the first aspect, the MBFO means comprise:
an optical element configured for generating a set of identical images;
a filter array means configured to spectrally filtering said image replicas, so that light is transmitted and/or reflected at a set of discreet spectral bands;
a glass screen configured for visualizing the filtered set of replica images; and
a relay lens configured for focusing the image displayed on the glass screen onto the at least one imaging sensor.

According to embodiments of the first aspect, the MBFO means comprise a universal mount means for detachably mounting the MBFO means with the corresponding lens adapter of commercially camera means, said camera means being either autonomously standing or integrated into mobile telephone/computer platform means.

According to embodiments of the first aspect, said IHA comprises an image-shifting compensation optical element disposed in the image path ending to the focal plane of the optical imaging means, the image shifting compensation optical element is configured to be positioned by the tilting actuator at a proportional and opposite tilting angle with respect to the tilting angle the ADSF-type filter so as to compensate for the tilting-induced optical medium pathlength variations and for the associated image distortion/displacement effects.

According to embodiments of the first aspect, the image shifting compensation optical element is a glass plate having a predetermined thickness and index of refraction that is selected such that the focused image is displaced in the opposite direction by a substantially equal distance to the displacement caused by said ADSF-type filter.

According to embodiments of the first aspect, the hybrid spectral imager is configured to operate as an expanded color gamut, metamerism-free and full spectrum photography camera, wherein:
the MBFO means and MFA sensor arrangement means are configured to capture at least five said single band images within the visible part of the spectrum; and the CPU unit is configured to execute a training task of a spectral estimation model on the basis of a large collection of spectra comprising, at least in part, a Munsell spectral collection; execute a spectral estimation model-based algorithm for fitting sparsely sampled spectral data points for reconstructing the spectra in all image pixels; calculate CIE-colorimetric color parameters from said spectra; and display in the display means a color image with pixels values corresponding to color parameters derived from full spectra.

According to embodiments of the first aspect, the MBFO means and MFA sensor arrangement means are configured to capture at least five single band images within the visible part of the spectrum and at least one single band image in the near infrared sensitivity range of said silicon sensor means; the CPU unit is configured to utilize the single band image near infrared response for executing image processing tasks with said processing output comprising at least in part: estimation of the spectral characteristics of the ambient light illuminating said target scene or object; estimation said target scene's or object's surface reflectance for achieving color constancy; extraction of haze elements from said color image.

According to a second aspect of the present invention, a method for video, full resolution hyperspectral imaging is provided, the method comprising the steps of:
obtaining a population of densely sampled optical spectra, statistically sufficient for representing the spectral identity/complexity of a target scene or object; analyzing said set of densely sampled optical spectra for extracting a sparse representation of said spectra population through spectral feature extraction; identifying, in the densely sampled optical spectra, critical spectral bands (CSB) corresponding to bands substantially overlapping with spectral bands being highly populated with prominent spectral features; and performing, by means of a hybrid spectral imager according to embodiments of the first aspect of the present invention, the steps of: capturing substantially simultaneously spectral images with center wavelengths corresponding to the identified CSB; reconstructing a spectral cube for a target object or scene by estimating the missing spectral data points and the corresponding spectral images though the fitting of the CSB spatial and spectral data points with a spectral estimation model associated with a spectral data-set sample of densely sampled optical spectra; and displaying at least one of the full content of the reconstructed spectral cube and the derived spectral thematic maps at video rates.

Scanning spectral imagers generate several dozens of spectral images at full spatial resolution, requiring however significant acquisition time. Snapshot spectral imagers generate also several dozens of spectral images, requiring zero scanning time, with some of them compromising spatial resolution and some others requiring long prost processing times not allowing for live spectral imaging.

An ideal hyperspectral imager may be described as an apparatus capable of acquiring and displaying the full content of a hyperspectral cube comprising 30 or more, narrow band images and/or any image means comprehensively representing said cube's content, nearly at video rates and at high definition sensor's resolution. The present invention seeks to approach this ultimate goal by enabling snapshot video spectral imaging at a desirable set of prominent spectral bands, which is complemented with a training-based spectral estimation for reconstructing the missing spectral images, such that the full content of said hyperspectral cube to be displayed at a video rate.

Particularly, the foundations of the present invention are found in the observation that the reflectance/transmission/fluorescence spectra of solid/liquid materials that are recorded in the sensitivity spectral range of the commonly used silicon or germanium light sensors (0.3-1.7 µm) are broad and have a small number of prominent features (such as peaks, valleys and slopes). This allows for the capturing of the spectral information at sparse sampling points laying in the vicinity of said prominent spectral features, since the information corresponding to the featureless portions of the spectra is largely redundant. This way, a number of spectral feature-informative spectral bands can be selected for simultaneous spectral imaging at full sensor's spatial resolution. The missing data points can be estimated on the basis of said spectral feature-informative spectral bans combined with an efficient training process. For a given spatial resolution, the maximum number of spectral bands that can be acquired/displayed nearly at video rates is determined by the bandwidth of the data transfer protocol. The today's available bandwidth reaches values as high as 20 Gbit/s (e.g. USB 3.2), allowing for several dozens of high-resolution spectral images (e.g. full HD or 4K) to be transferred at video rates or even faster. In practical terms, the number of said prominent spectral features is typically less than ten, indicating that the bandwidth sets no significant restrictions to the number of multi-megapixel spectral images that can be acquired simultaneously and nearly at video rates.

The intensity values at a given pixel location of said snapshot spectral images are captured at different wavelengths and comprise the sampled spectral information. As discussed earlier, the sampled data points are informative (although sparse) for the prominent features (e.g. peaks, valleys) of the spectra. The sampled data points can therefore be fitted with a spectral estimation model, trained with a suitable data set, for restoring a complete spectrum for every image pixel. This corresponds to reconstructing a complete spectral cube comprising both sampled and estimated spectral images.

Notably, estimation of broad and smooth spectra is a fast and much more straightforward procedure, as compared to the estimation of missing spatial points in pixelized spectral imagers, with the latter comprising a typical prior art practice. As discussed previously in this paragraph, said spectral estimation accuracy increases remarkably when the acquisition spectral bands lay in the vicinity of the wavelengths corresponding to said prominent spectral features. The wavelengths corresponding to said prominent spectral features may in general, vary depending on the nature of the imaged subject category (e.g. plants, skin, food etc.). For the purpose of enabling the adaptation to this variation, the disclosed hybrid spectral imager integrates electro-optic means allowing for tuning and locking simultaneous spectral image acquisition at set of Critical Spectral Bands (CSB). Said single CSB have typically a narrow (e.g. 10-40 nm) Full Width at Half Maximum (FWHM) and center wavelengths laying in the close proximity with the wavelengths corresponding to said spectral features. Upon selecting and locking said CSB, a set of narrow band images are captured simultaneously and displayed at video rates. At an execution time comparable to a video refresh rate, training-based spectral estimation procedures are employed for restoring the missing spectral data points, using as basis said CSB images. Finally, the resulting spectral cube is a mixture of estimated and acquired (CSB) spectral images.

As discussed earlier, spectral estimation require a priori knowledge with regard to the expected spectral characteristics of said target scene or object. The present invention provide means for establishing such an a-priory knowledge in case that it is missing. In this case, the disclosed hybrid spectral imager switches into the scanning mode, where a series of spectral images are collected in time succession, composing the sampled spectral cube. Said sampled spectral cube my comprise an a-priory knowledge with regard to the expected spectral characteristics of said target scene or object for subsequent imaging tasks. The same dataset may be also analyzed for the purpose of identifying said prominent spectral features and the corresponding CSB for subsequent snapshot/spectral estimation operation and for developing a reliable spectral estimation model.

Spectral estimation may be based on a generic or an application-specific training set and relevant algorithms may be fast enough, requiring negligible post processing time. The output data stream of the disclosed hybrid spectral imager corresponds to a complete spectral cube, the full content of which may be displayed at video rates.

The present invention discloses miniaturized tunable filter solutions, enabling hybrid, scanning and snapshot operation. The spectral filtering of the acquired spectral images is obtained with the aid of Multi-Band Filtering Optics (MBFO). Said MBFO comprises beam divider means for generating at least two replica images of the target image; and tunable multiband filtering (TMF) means interposed into the imaging path and effecting a tunable multi-bandpass filtering in said images replicas; Said MBFO effects a first spectral filtering of the wavelength content of an image of a scene. Said MBFO may comprise optical elements comprise at least in part bean dividers selected from a group of optical elements including but not limited to cube beam splitters, plate beam splitters, polarizing beam splitters, pentagon beam splitter/dividers, right angle prism with mirror coated legs, mirror coated pyramid prisms with mirror-coated legs, polka-dot beam splitters and pellicle beam splitters. or combinations thereof. Said MBFO comprise also tunable multiband filtering (TMF) means comprising, at least in part, angle depending spectral filtering (ADSF), ADSF-type dichroic and polychroic mirrors, ADSF-type multi-bandpass filters, spatial light modulators, acousto-optic, liquid crystal spectral modulators, surface plasmons filters and combinations thereof. Said MBFO effects an image multiplication generating a number of image replicas, which replicas are subsequently subjected to a multiband filtering by said TMF. Said TMF may be tunable allowing for the acquisition/capturing of a set of multiband images at a given tuning step and/or a full spectral cube comprising at least thirty (narrow) single images band images with full width at half maximum (FWHM) in the range 10-40 nm. ADSF-type filters, for example, have the property of varying the center wavelengths of the transmitted/reflected bands by tuning upon varying (tilting) the angle between the normal to their surface and the incoming chief imaging ray. This property is exploited in certain embodiments of present invention to enable both snapshot multiband and scanning spectral imaging. Said MBFO may be disposed either in front of an objective lens means, or in the space between the objective or (rely) lens flange and the focal plan of the imaging optics. Said multiband filtered replica images are captured with an image sensor arrangement comprising a number of mosaic filter array (MFA)-filtered focal plane array (FPA) sensors. Said imaging sensor arrangement means comprise at least one imaging sensor, equipped with a mosaic filter array (MFA). Said MFA masks, in a pixelized manner, said FPA sensor with at least three wide-band primary color-type filters, with each primary color-type response separating and capturing one single-band image component from said multiband-filtered image replicas.

The spectral transmission characteristics of said MFA is substantially broader than the FWHM of the spectral bands transmitted or reflected by said MBFO. Moreover, the TMF multiband filtering generates a set of single bands separated by blocking spectral regions with substantially greater spectral width with said single band images. This way, each said single band is tuned and captured within the corresponding primary color response, comprising also the means for separating the multiband spectral content of said replica images into a set of narrow, single band images. Said MFA is selected from a group comprising at least in part red-green-blue (RGB) MFA used in color cameras, RGB-IR (infrared) MFA and multiband MFA (pixelized spectral imaging sensors). At a certain configuration, said MBFO may transmit, for example, 3 or more narrow spectral bands and may reflect, for example, 3 or more different or (spectrally) complementary to the former narrow spectral bands. In one embodiment of present invention, comprising two MFA-FPA imaging sensors, one is disposed at the focal plane of the reflected from said MBFO imaging rays and the other is disposed at the focal plane of the transmitted from said MBFO imaging rays. In the of embodiments employing, for example, said ADSF-type filtering, by setting a certain tilting angle, said MBFO transmits/reflects at least six spectral bands whose FWHM is selected to be much narrower than the FWHM of the masking filters of said MFA. This way, the narrow band components of the MBFO output image are (substantially) separated by the MFA, with each said MFA broad-band filter transmitting a certain said narrow band component, at their spectrally overlapping wavelength range. By assuming an MFA with at least three different said masking filters, at least six narrowband images can be acquired/captured simultaneously by sensor arrangement comprising two-FPA imaging sensor and at video rates. Upon changing the tilting angle of said ADSF, a new set of narrow band images can be instantly acquired and displayed.

The present invention provides actuator means for controlling the tilting angle of said ADSF. The tilting of ADSF allows for the adaptation of the multiband image acquisition wavelengths to said CSB. It also allows for switching to said scanning operation by tilting said ADSF with a series of steps, so that the transmitted spectral bends are shifted covering the entire operational wavelength range. In every tilting step, a set of spectral images are captured in a snapshot fashion until acquiring a complete said sampled spectral cube.

The disclosed electro-optic arrangement comprising the hardware of said hybrid spectral imager has the advantage of enabling miniaturization. The overall size of said hardware is largely determined by the size of said imaging sensor means, making miniaturization possible. Tilting actuators can be easily miniaturized by employing MEMs actuators such as magnetic, electrical, thermal actuators, etc. Apart from that, the power requirements are low, especially when operating in the snapshot mode, which is the case in routine uses in a given application field. The disclosed hardware of said hybrid spectral imager can therefore be integrated or interfaced into mobile phone or computer platforms, without significantly increasing their end user price.

The disclosed hardware setup is complemented with machine learning, artificial intelligence, spectral channel cross talking reduction methods, data visualization and labeling. These algorithms are executed in data processing module, which is an integrated part of present invention.

The present invention discloses also means for visualizing spectral cube data in a comprehensive manner. Unsupervised and supervised spectral cube clustering algorithms produce spectral maps, which at certain circumstances are displayed side-by-side with color images in real time for comparison and documentation.

In one preferred embodiment the spectral cube data or the said cluster class centroids are compared with labelled reference spectra for converting said color-coded spectral map to a diagnostic or a chemical imaging map. This way, said diagnostic or chemical map is used for obtaining information with regard to a tissue pathology, food quality etc., or for obtaining structural and compositional information.

In another embodiment of present invention, the spectral estimation training data-set is obtained from spectral data bases including spectra that correspond to a long list of natural and artificial colors, such as the Munsell data base. In that case, the calculated full spectra are multiplied with the CIE's standard observer responses and with the standard illuminant's spectral power distribution and, finally, are all integrated over the visible part of the spectrum, to provide standardized color indices for every image pixel. In this embodiment the disclosed hybrid spectral imager operates as a spectral photography camera with substantially improved color gamut, also enabling mesmerism-free photography.

In yet another embodiment the disclosed hybrid spectral imager offers spectral sensitivity extended to the near infrared (NI R) portion of the spectrum. Relaying on the fact that natural and artificial illuminants have distinct spectral characteristics in the NIR band, NIR sensitivity is exploited for the disentanglement of the illuminant's spectral power distribution from the target's surface reflectance. This provides a means for estimating the surface reflectance of a target, an essential aspect for achieving color constancy in digital photography.

Referring, finally, to the application field of the disclosed hybrid spectral imager these include (but not limited to) nondestructive testing, spectroscopy, microscopy, endoscopy, tissue analysis, artificial/robotic vision, vision of autonomous machines, quality control, remote sensing, lab-on-a-chip tests, expanded gamut photography, metameric and haze-free photography, chemical imaging and in vivo pathology mapping

BRIEF DESCRIPTION OF THE DRAWINGS

The following detailed description of the embodiments of the present disclosure will be better understood when read in conjunction with the accompanying drawings. For the purpose of illustrating the disclosure, there is shown in the drawings embodiments which are presently preferred. It should be understood, however, that the present disclosure is not limited to the precise arrangement and instrumentalities shown.

FIG. 1A shows accurately (RMSE: 1.1-1.6) estimated spectra due to the proper selection of said CSB as wavelengths corresponding to said spectral features. FIG. 1B shows a spectral estimation result with poor accuracy (RMSE: 10.3-23.0) due to improper selection of said CSB failing to capture significant spectral features.

FIG. 5B illustrating a similar embodiment, wherein said beam divider is a prism with its two sides being mirror coated, and FIG. 5C showing an MBFO optical arrangement comprising one tilting plate beam divider or one tilting polychroic mirror or one tilting multiband-pass filter disposed in the imaging ray path and one tilting uncoated glass plate, disposed in the same imaging ray path, compensating for image shifting artifacts.

FIG. 6A illustrates said MBFO comprising a modified Köster prism which is disposed substantially over the active area of single said MFA-imaging sensor; FIG. 6B depicts yet another embodiment of present invention according to which a microlens array refocuses the image formed at the focal plane of said objective lens optics, forming a set of identical images (image multiplication) onto a glass screen after passing through a multiband pass filter array; and FIG. 6C depicts yet another preferred embodiment wherein said MBFO comprises a dual (or more) channel objective lens optics, with each channel being filtered by two said complementary multi-bandpass filters.

FIG. 8A shows the combined responses of said MBFO and said MFA; FIG. 8B shows the spectral profile of the resulting raw narrow single images resulting from the double filtering of the incoming image effected by both MBFO and MFA image; and FIG. 8C shows the spectral profile of the resulting narrow band images, processed to remove the spectral "tails" of MFA entering the MBFO narrow bands, across the spectrum.

FIG. 10A depicts a training process involving a comparison attempting the best match between the samples generated by a k-number CSB acquisition (test sample) and a training set comprising M spectra with N sampled data points (training set); and FIG. 10B illustrates schematically the spectral estimation after establishing said estimation matrix, with the aid of which, the k-sparse data points are converted to a full spectrum.

DETAILED DESCRIPTION OF THE INVENTION

Figure 1A:
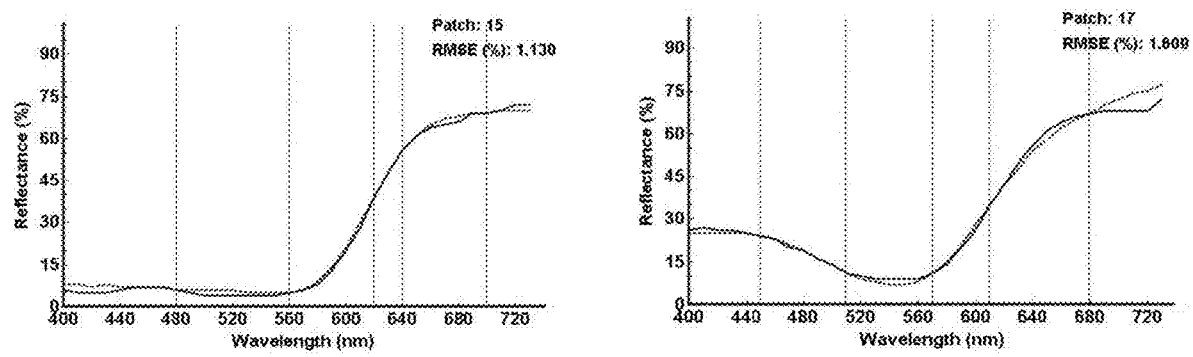
FIGS. 1A-1B shows the comparison of densely sampled spectra (solid lines) with estimated spectra, derived sparse said CSB (vertical lines) sampling data and an estimation model. The data have been obtained from the Macbeth color checker standard sample. The Root Mean Square Error (RMSE) (%) is used as a spectral similarity metric.

For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The system and method are described with respect to the embodiments of the present invention provide acquisition of images containing both spatial and spectral information of the imaged object. According to the analysis of prior art, provided in the relevant paragraph, there are two main categories of spectral imaging systems, namely, the scanning and the snapshot spectral imagers. The present invention teaches reconfigurable hybrid spectral imagers that can operate either in the scanning or in the real time snapshot mode.

An example of practicing the present invention in microscopy shows the advantages of said hybrid spectral imager over prior art. In pathology/histology, for example, tissue samples are stained with a variety of contrast enhancing chromophores or fluorophores for facilitating the visualization of features of diagnostic importance. However, the spectral overlapping of the stains employed makes their separate observation a difficult task. Separate mapping of the per-pixel concentration of multiple fluorophores/chromophores emerges as an advanced assay, holding the promise to improve diagnostic outcomes in pathology. Spectral imaging offers a solution to this problem through the steps of a) measuring a full spectrum per pixel; b) developing a stain mixture model with the a-priori knowledge of the so-called end-member spectra of the isolated stains; c) calculating the so-called abundances as quantitative indices of the relative concentrations of the stains in the mixture. However, when employing a scanning spectral imager, the associated scanning time is cumulatively significant, given that a great number of regions of interest in the examined samples. Adding conventional spectral imagers to routine procedures will unavoidably have a negative impact to the workflow of pathology procedures, which comprise a barrier to their market entry. Adopting a prior art snapshot solution on the other hand, is also a suboptimal solution due to long prost-processing time required for reconstructing the spatial or spectral data points. More specifically, in conventional snapshot systems the post-processing algorithms that are employed for expanding data dimensionality yield data processing times exceeding the acquisition times required by scanning spectral imagers.

The advantages of the disclosed hybrid spectral imager over prior art systems are illustrated below using the microscopy application as an indicative example. When no a priori knowledge exists with respect to the spectral characteristics of the tissue pathology-specific stains, the disclosed hybrid spectral imager will initially switch to the scanning mode and will collect a complete spectral cube. Next, the processing unit integrated or interfaced with said hybrid spectral imager, will analyze said complete spectral cube data and will estimate the minimum set of sparse spectral data, that comprehensively describes and without significant loss the acquired raw spectra of said complete spectral cube. This process corresponds to removing the redundant information from the sampled data set. Due to the broad nature of the spectra acquired in the spectral band 300 nm-2500 nm, said minimum set of sparse spectral data vary in a range of 5-10 discrete wavelengths. This is an experimental finding is an integrated part of this disclosure and has derived from the analysis of publicly available spectral databases. This characteristic applies to the vast majority of solid and liquid materials, with number of the informative wavelengths to depend on the complexity of the sample. Estimation, through a microprocessor unit, of the minimum number or the most informative wavelengths, named here as CSB, is, by nature, an optimization problem addressed with relevant algorithms. Said optimization refers to spectral features that are extracted with feature extraction algorithms, such as discrete wavelet transform or similar methods. The aforementioned analysis feeds the system's control unit with the request to configure said MBFO so that said hybrid spectral imager acquires the identified said CSB. This task is executed by instructing the actuator(s) to tilt said multiband sensor filtering means and to lock them at the proper angle. Upon completing this self-configuration procedure, the system switches to the real time snapshot mode of operation or, in other words, to the video spectral imaging operation. Besides providing the basis for selecting the CSB, the spectral data collected during the scanning operation mode are used, at least in part, as a training set for performing spectral estimation. Finally, with the system configured to operate in the video spectral imaging mode, the CSB are captured instantly, while the missing spectra data points are estimated fast-enough so that the complete spectral cube images are becoming available for display at video rates (e.g. 25 f/s). This kind of data availability allows for the calculation of said stain concentration maps to become available at a nearly real-time refresh rate. This way, said hybrid spectral imager might improve the diagnostic outcomes in pathology/histology without compromising the workflow.

Another application example showing the distinct advantages of said hybrid spectral imager is endoscopy. Here, both the endoscope's tip and the examined organ(s) are in continuous random motion, implying that said video spectral imager comprises a unique solution for enabling real-time, full spatial and spectral resolution spectral imaging in endoscopy. In this case, said CSB are identified through the correlation of spectral data with the outcomes of a reference diagnostic method. Said reference diagnostic method may include, for example, clinical evidence or biopsy/histology or molecular analyses of combinations thereof.

Figure 1B:
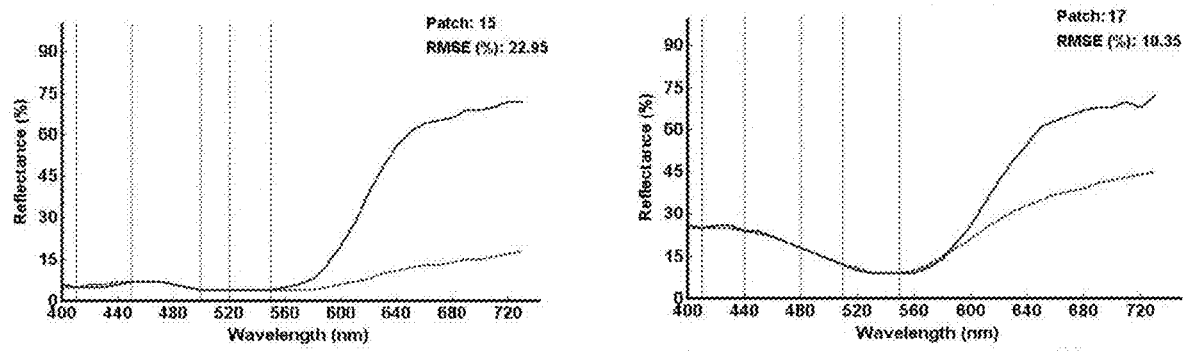

Reference now is made to FIG. 1 which depicts spectra obtained from the Macbeth color checker standard sample. The solid lines correspond to spectra acquired by a commercial scanning hyperspectral imager, which are used here as reference. The dashed lines correspond to estimated spectra using as basis six CSB. The center wavelengths of said CSB are marked as vertical lines on the plots. FIG. 1A shows estimation curves based on properly selected CSB, so that the sparse snapshot samples correspond to both valleys and peaks. As it can be seen, the estimation accuracy is quite high, which evidenced by the low value of Root Mean Squared Error (1.1-1.6%). FIG. 1B illustrates the case where said CSB have been selected at wavelength bands not strictly corresponding to said spectral features. In that case, even though the spectral estimation algorithm is the same as in FIG. 1A, its accuracy in predicting the spectrum is poor (RMSE=10.3-23.0%). These findings comprise the motivation for the solutions provided in present invention. Particularly, present invention claims a hybrid reconfigurable and adaptable real time snapshot spectral imager, where said CSB are tunable to adapt to the wavelengths corresponding to said spectral features for increasing spectral estimation accuracy.

All possible electro-optic solutions that are enabling the tuning and the adaptation of said CSB for multiband snapshot operation, while in parallel improving said spectral estimation accuracy comprise an integrated part of this disclosure. Both electro-optic and algorithm means that are described below comprise preferred only embodiments for achieving simplicity, low cost, volume and power consumption, which are critical figures when mobile applications are considered.

Figure 2:
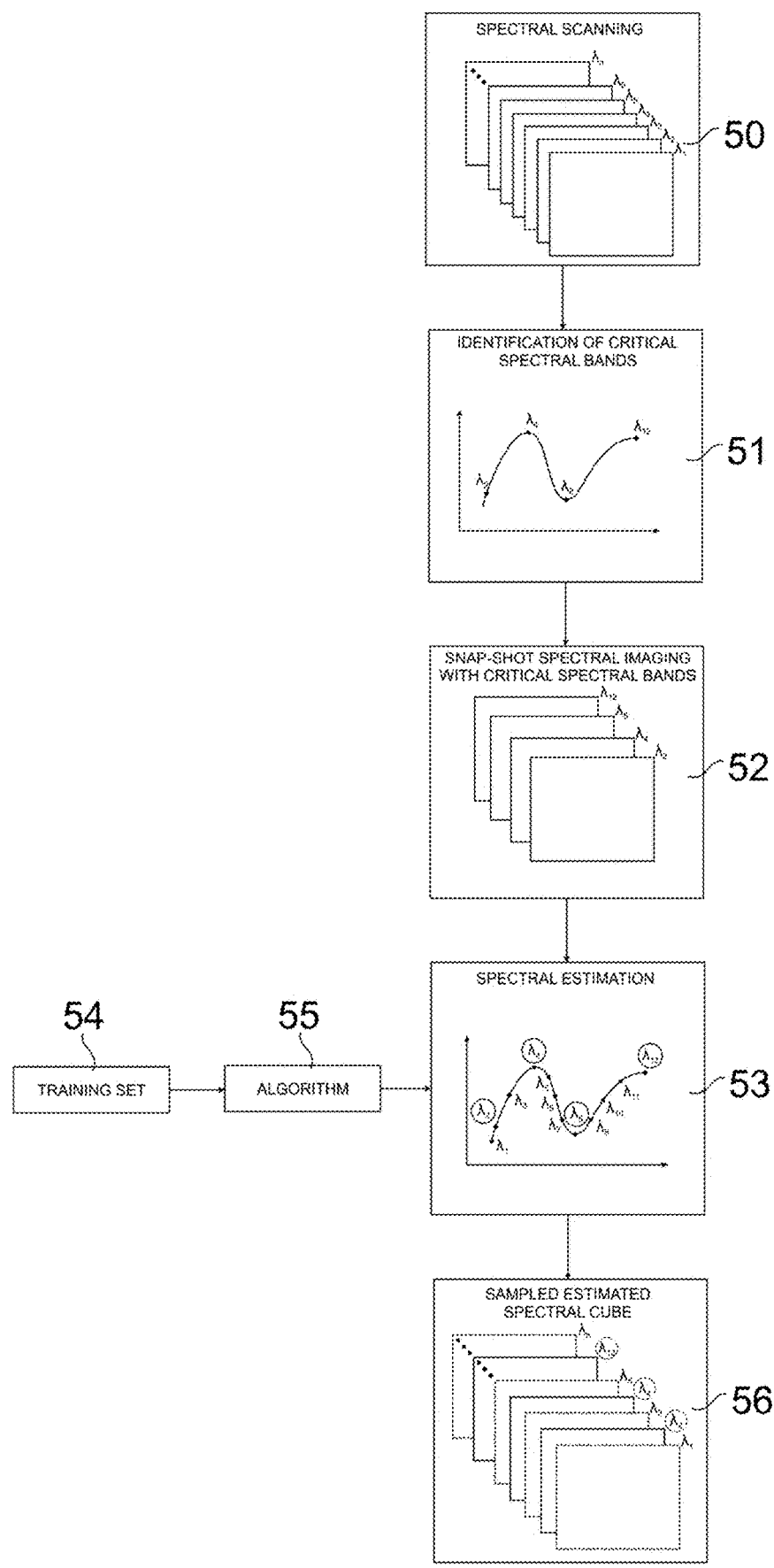
FIG. 2 schematically depicts the hyperspectral imaging method implemented in the disclosed hybrid spectral imager according to which snapshot video spectral imaging at a desirable set of prominent spectral bands is complemented with a training-based spectral estimation for reconstructing the missing spectral images, such that the full content of said hyperspectral cube to be displayed at a video rate.

The descriptions below disclose method concepts and together with embodiments with preferable imaging head arrangements (IHA) comprising said MBFO means, said MFA-imaging sensor array means, tilting actuator means and optical imaging means, all together implementing said hybrid spectral image acquisition. Reference now is made to FIG. 2, which schematically depicts the basic aspects and concepts of the disclosed hybrid spectral imager. With said IHA instructed to operate in the scanning mode, sets of e.g. 5-10 spectral images are captured simultaneously in every tilting step and for a number of tilting steps, until scanning the entire operation spectral range, e.g. 400-1000 nm in the case of using silicon sensor array means. This way, the scanning operation mode of the disclosed hybrid spectral imager collects said sampled spectral cube 50 in a fast and dense sampling process. The "densely sampled data set" term is defined herein as a sampling procedure involving a tuning step of the center wavelength(s) in the range of 5-10 nm resulting in a collection of at least 30, spectrally successive single band images. The term "sparsely sampled data" is defined herein as sampling procedure involving the capturing of 5-10 images at discrete wavelengths.

It is worth noticing that capturing sets of spectral images in every tuning step instead one-by-one has a clear benefit over prior art scanning devices, since scanning time is remarkably reduced. Said sampled spectral cube contains one full spectrum per image pixel, with their total number equaling to the spatial resolution of said MFA-sensor arrangement means. Identification of said spectral features in the millions of spectra contained in said sampled spectral cube may be performed automatically. One such a method, which is incorporated here as an example, involves an unsupervised clustering of said sampled spectral cube spectra, which returns a limited number (typically 5-15) of cluster centroids. Said cluster centroids are representative of the identified distinguishable spectral classes and therefore the analysis for identifying said spectral features could be limited to the analysis of said centroid spectra. Analysis may involve automatic feature extraction algorithms for identifying said prominent wavelengths corresponding, for example, to peaks, valleys, slopes etc. The analysis is concluded when the minimum number of 5-10 discrete and most informative spectral bands have been identified. Based on said spectral feature extraction, said MBFO is configured to acquire a set of images at the CSB 51, in a real time snapshot operation 52. It is obvious to one skilled in the art that said CSB and said spectral feature wavelengths may vary in different scenes or target objects. Therefore, steps 50 and 51 provide steps for the adaptive (re-) configuration of said MBFO.

A thorough analysis of generic and application-specific spectral databases in the spectral band 400-1000 nm has concluded that said minimum set of sparse spectral data, depicting the vast majority of spectral features, vary in a range of 5-10 discrete wavelengths for the whole content of said databases.

As discussed earlier, the dense (high sampling rate) spectral information obtained from said hybrid spectral imager operating in the scanning mode combined or not with generic or application-specific spectral databases are used as a training data set 54 of said spectral estimation algorithm means 55. Relying on said training set, machine learning and artificial intelligence algorithms are employed for predicting the missing data-points in the spectra collected with snapshot sparse spectral imaging, with the resulting reconstructed full spectrum comprising a mixture of sampled and estimated data points 53. From these full spectra data points, estimated for every image pixel, a complete spectral cube may be obtained, comprising both said sampled and said estimated spectral images. Properly trained spectral estimation procedures may be fast enough, with execution times lying in the millisecond regime, even for spectral cubes comprising several full HD spectral images. This implies that upon establishing a set of said CSB for a particular application, for example human, animal, or plant tissue diagnosis, then full spectral cubes can be collected nearly at video rates, thus removing said tradeoffs between spatial-spectral information and image display refresh rate.

In the next paragraphs, a number of embodiments will be disclosed referring to said imaging head arrangement (IHA) of said hybrid spectral imager.

The present invention discloses miniaturized tunable filter solutions, enabling hybrid, scanning and snapshot operation. The spectral filtering of the acquired spectral images is obtained with the aid of Multi-Band Filtering Optics (MBFO). Said MBFO comprises beam divider means for generating at least two replica images of the target image; and tunable multiband filtering (TMF) means interposed into the imaging path and effecting a tunable multi-bandpass filtering in said images replicas; Said MBFO effects a first spectral filtering of the wavelength content of an image of a scene. Said MBFO may comprise optical elements comprise at least in part bean dividers selected from a group of optical elements including but not limited to cube beam splitters, plate beam splitters, polarizing beam splitters, pentagon beam splitter/dividers, right angle prism with mirror coated legs, mirror coated pyramid prisms with mirror-coated legs, polka-dot beam splitters and pellicle beam splitters. or combinations thereof. Said MBFO comprise also tunable multiband filtering means comprising, at least in part, angle depending spectral filtering (ADSF) bands pass filters, ADSF-type dichroic and polychroic mirrors, ADSF-type multi-bandpass filters, spatial light modulators, acousto-optic, liquid crystal spectral modulators, surface plasmons filters and combinations thereof. Said MBFO effects an image multiplication generating a number of image replicas, which replicas are multiband filtered and simultaneously acquired. Said multiband filtering may be tunable allowing for the acquisition/capturing of a set of multiband images at a given tuning step and/or a full spectral cube comprising at least thirty (narrow) single images band images with full width at half maximum (FWHM) in the range 10-40 nm. ADSF-type filters, for example, have the property of varying the center wavelengths of the transmitted/reflected bands by tuning upon varying (tilting) the angle between the normal to their surface and the incoming chief imaging ray. For example, an ADSF-type multiband reflection and/or transmission filter, have the property of tuning at about 15% the bands' center wavelength, when it is tilted within an angle range of ±30°.

This property is exploited in certain embodiments of present invention to enable both snapshot multiband and scanning spectral imaging. Said MBFO may be disposed either in front of an objective lens means, or in the space between the objective or (rely) lens flange and the focal plan of the imaging optics.

Figure 3:
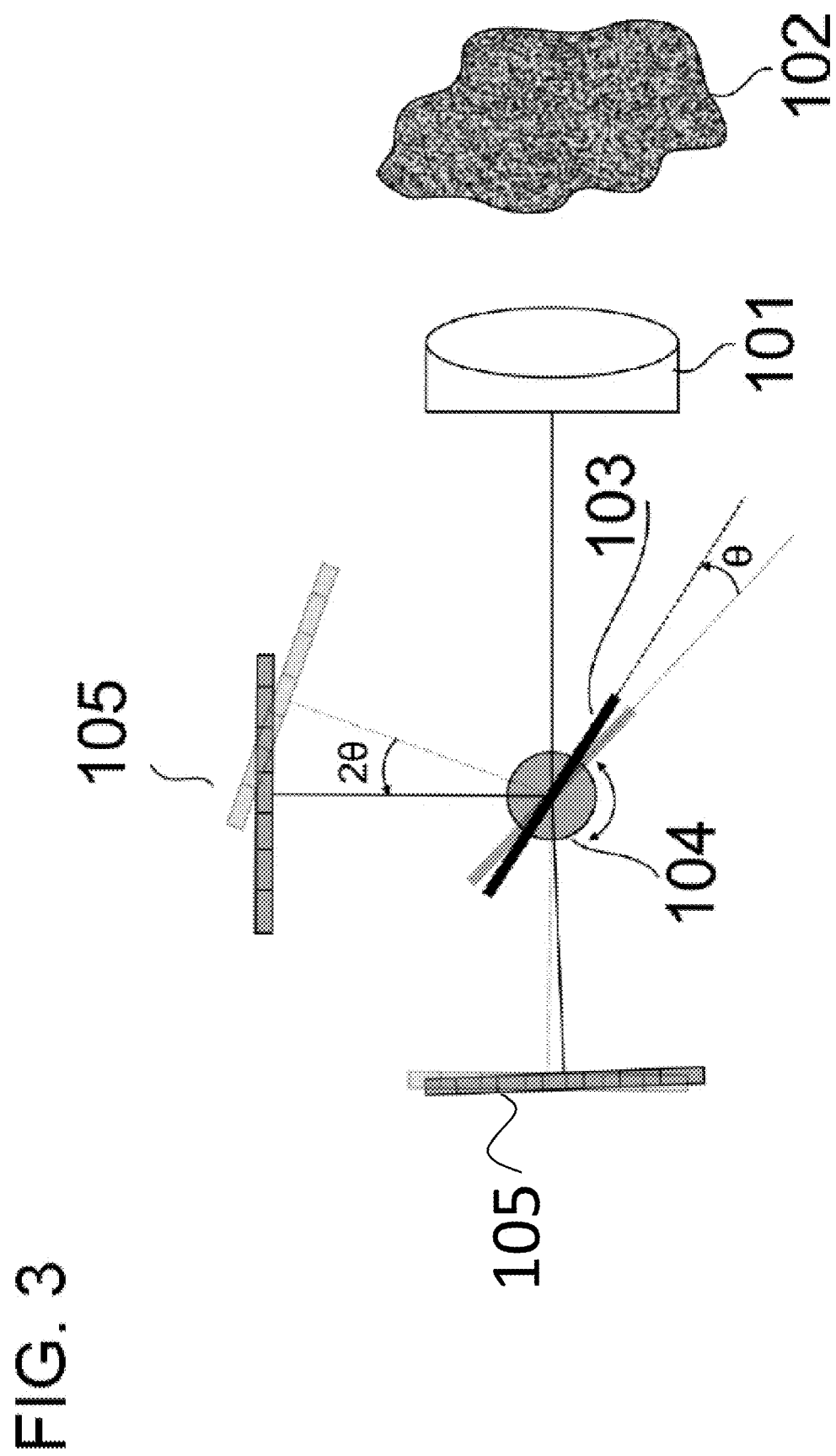
FIG. 3 illustrates a prior art arrangement with said MBFO comprising a tilting polychroic mirror arrangement.

Reference in now made to FIG. 3, which illustrates an arrangement with said MBFO comprising a polychroic mirror. This category of optical filters is predominantly used in fluorescence microscopy for separating excitation/emission channels in fluorescence imaging. In typical microscopy systems, said excitation/emission channels form an angle of 90 degrees, with said polychroic mirror being disposed at the junction of said channels forming a fix 45 degree angle. The majority of narrow-band reflecting or absorbing filters, including said polychroic mirror, have the property of shifting the transmitted/reflected center wavelength(s), when the angle between their surface and chief incoming ray changes. This comprise the basis for developing tunable filter arrangements using such bandpass filters. However, as far as said tunable plate filters are considered for imaging applications, there are two main drawbacks that make their standalone use problematic, namely: a) when said dichroic mirror is tilted by an angle θ, the reflected ray is tilted by an angle of 2θ. Diffraction angle also change with angle θ but at a lesser degree; b) the reflections originated by the back surface of said dichroic mirror, generate double image artifacts known as ghost image effect, which comprise a source of artifacts in the reflected image. FIG. 3, illustrates an IHA comprising objective lens optics 101 configured to focus the image of a target object or scene 102 onto the surface of an image sensor array means 105. The sensor array means may be a mosaic filter array (MFA) sensor arrangement comprising at least one MFA-focal plane array (FPA) sensor. A polychroic mirror plate 103 is disposed in the imaging ray path, which reflects and transmits multiband filtered imaging rays. In certain preferred embodiments, at least two sets of different multi-band filtered imaging rays are generated and directed to MFA sensor arrangement comprising two FPA sensors. In these cases, the center wavelength of the transmission bands of a first set of said multiband filtered imaging rays may be correspond to blocked bands of a second multiband filtered imaging rays. This way said multiband-filtering corresponding to the two imaging sets have preferably complementary center wavelengths for ensuring evenly distributed spectral sampling. The images corresponding to these two branches are captured by said MFA sensor arrangement comprising two FPA imaging sensors 105. As it can be seen, the angle depending spectral filtering (ADSF) means is a polychroic mirror plate 103, secured onto a tilting actuator axis 104. Said tilting actuator is configured to adjust the tilt angle, and consequently the direction of the imaging ray beams, of the polychroic mirror. For example, the polychroic mirror is configured for filtering the image captured by the objective optic means, such that imaging rays are transmitted and reflected at specific spectral bands with a narrow spectral bandwidth e.g. 10-40 nm. The filtered images emerging from the polychroic mirror are subjected to a second filtering by the mosaic filter array (MFA) sensors, which comprises an array of broad-band masking filters each configured for transmitting imaging rays at a specific spectral band. The spectral bands of the masking filters are selected to have a broader bandwidth at Full Width at Half Maximum (FWHM) compared to the bandwidth at FWHM of the polychroic mirror spectral bands. In this way, each masking filter is arranged to transmit images from an overlapping polychroic mirror spectral band. As a result, the masking filter is configured for substantially separating the narrow band images emerging from the polychroic mirror before they are captured by the imaging sensor array and processed by a processing unit for the generation and display of a spectral cube associated with the target sample or scene. With the present invention multiple narrow band images are simultaneously captured by the image sensors at the selected multiband spectral filtering defined by the polychroic mirror. In order to create the spectral cube for the target sample or scene the spectral information from the missing spectral bands may be estimated by the processing unit on the basis of the captured spectral information and/or a training spectral data set. As previously described, the center wavelength of each polychroic mirror multiband filtering may be shifted, by adjusting the tilt angle of the polychroic mirror using the tilting actuator. For example, depending on the application, the processing unit may control the operation of the tilting actuator such that the angle of the polychroic mirror is adjusted and the center wavelengths of the multiband filtering caused by said polychroic mirror are shifted so that they fall in the proximity of a set of critical spectral wavelengths containing the prominent spectral features e.g. peaks, valley, slopes, of the target sample or scene under analysis. At each tilting step a new set of images are obtained simultaneously in snapshot mode. Similarly, the embodiment of the hybrid spectral imaging shown in FIG. 3 can be used in a scanning mode to scan the entire spectrum in order to create a complete spectral cube for the target sample or scene. For example, the processing unit may control the tilting image such that the angle of polychroic mirror is adjusted in small increments. In this way, the center wavelength of the polychroic mirror spectral bands may be shifted by small increments e.g. 5-10 nm until the entire target spectrum is scanned. In each tilting step, a set of images are simultaneously captured by the imaging sensor and processed by the processing unit to create a complete spectral cube containing spectral and spatial features of the target sample or scene under analysis captured at each sampled wavelength. In FIG. 3 and in all the embodiments of present invention that will be disclosed below, said objective lens optics means 101 are selected from a broad collection of imaging optics including but not limited to photography lenses, microscopy optics, collimating optics infinity corrected optics rigid or flexible endoscopes, and telescopes. Said target object 102 is selected from a group including but not limited to human or animal tissue, plant tissue, landscape scene, processed or raw food material, natural material, manmade material, in aerial, land or underwater imaging conditions. Said sensor array means are semiconductor focal plane arrays masked with said MFA. Said tilting actuator means 104 may be constructed at least in part using motion actuators/divers means selected from a list including but not limited to galvanic electromechanical elements, stepper motors, rotating solenoids, magnetic, electrical and thermal actuators. In certain embodiments of present invention, intended to miniaturized versions of said IHA, suitable for encapsulation into said mobile phone and computer platforms, said tilting actuator means is microelectromechanical system (MEMs) means. The disclosed arrangements may also include additional filters such as short or long pass optical filters for restricting the spectral sensitivity range of said sensor array means 105 to desired regions of the spectrum. It may also include optical elements for correcting the acquired images for image shifting, distortions, aberrations, ghost images, defocusing and in general, for optics-related artifacts.

The present invention discloses arrangements compensating for the aforementioned drawbacks of prior art. Particularly, said tilting actuator means may be mechanically coupled with a gearing system onto which said MFA sensor array means are affixed. According to present invention, compensation is achieved by rotating the first said image sensor means that captures the reflected image by an 2θ angle. The second said sensor array means that capture the refracted image is also rotated but by a much smaller angle. Rotation of first and second said imaging sensor means comprises a condition for maintaining the same field-of-view during spectral scanning. Rotation of said image sensor means is activated by and synchronized with said tilting actuator means 104 with the aid of a motion transferring gearing system (not shown).

According to present invention compensation for ghost images is achieved with said polychroic mirror comprising a coating deposited along the diagonal of cube beam splitter (not shown). Said coating is very thin, so that there is no second surface reflection. Other embodiments mitigating the ghost image problem include plate polychroic mirrors with antireflection coating deposited onto said back reflecting surface of said polychroic mirror plates 103 or said polychroic mirror plates 103 being constructed as a coating onto a polka-dot or pellicle substrate.

Figure 4A:
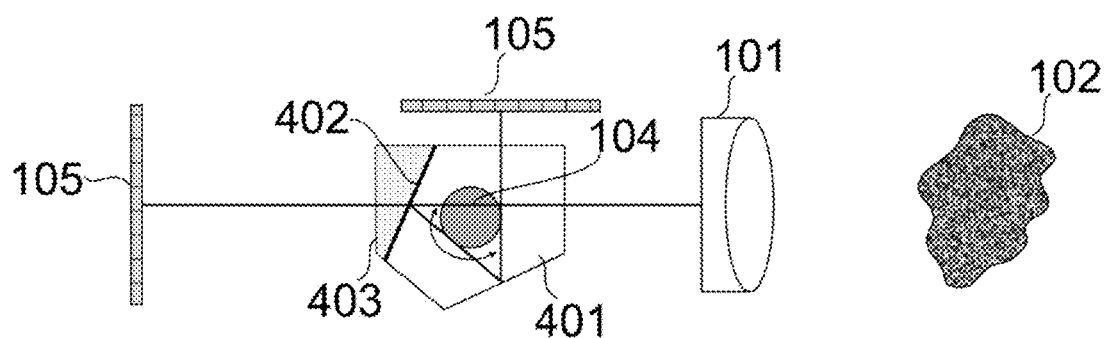
FIGS. 4A and 4B show one preferred embodiment of the present invention, with said ADSF comprising a modified tilting penda-prism beam divider, so that the two output substantially orthogonal beams are spectrally filtered to contain components with desirable spectral profiles.
Figure 4B:
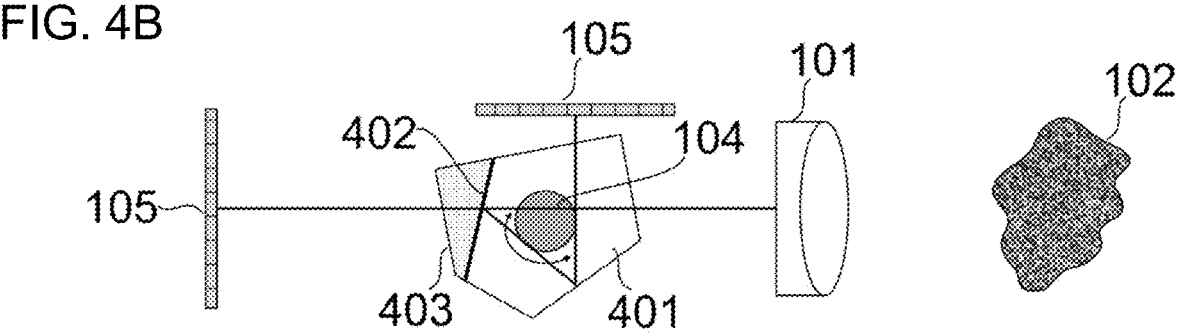
Figure 5A:
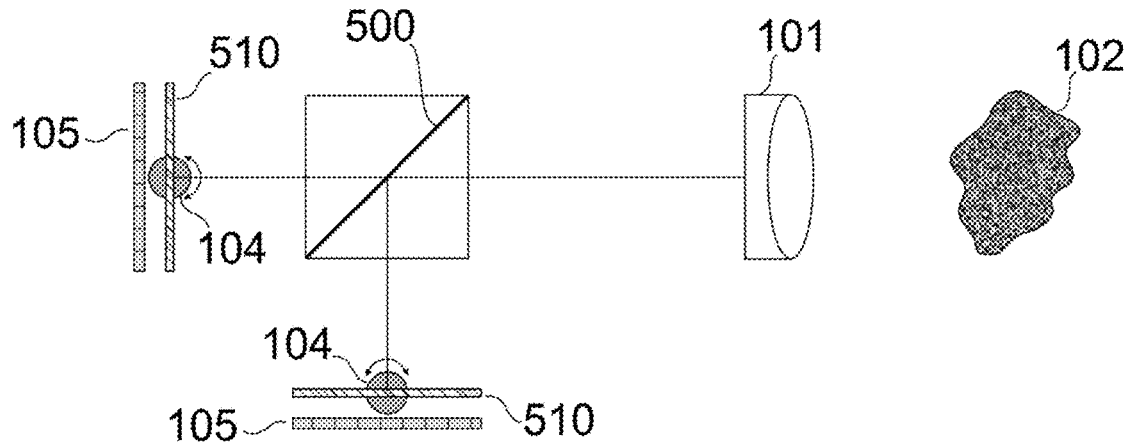
FIGS. 5A-5C show further preferred embodiments of the present disclosure, with FIG. 5A depicting said MBFO comprising a cube beam divider rested at a fixed position in the imaging path and two tilting filters effecting a tilting angle-depending spectral filtering.

Another more robust preferred embodiment of present invention employing polychroic mirror means is illustrated in FIG. 4. In FIG. 4A, said beam divider means of said MBFO is a penda-prism beam divider modified to have one of its five surfaces coated with a polychroic mirror substrate 402. Said penda-prism is further modified so that said coated surface is cemented together with a triangle prism 403 for the purpose of making the prism's rear surface parallel with the front. FIG. 4B depicts principle of operation and the main advantages of this embodiment. The double reflection of the incoming beam: one occurring in said polychroic-coated interface 402 and one in the uncoated or flat-mirror coated surface of said penda-prism, makes the direction of the emerging beam to remain practically unaffected from the prism's tilting caused by said tilting actuator means. This way, there is no need for gearing arrangements, something that simplifies the design and reduce volume and cost. Another advantage of present embodiment relates with the fact that that due to the thin film nature of said polychroic coating there is no double reflection effect that would introduce artifacts to said reflected image. Finally, within an operationally acceptable tilting angle range of said modified penda-prism, the transmitted rays are also unaffected by said tilting angle. It is obvious to one skilled in the art that variations of present embodiment, such as replacing said polychroic mirror with a couple multiband-pass filters, one disposed onto the pentaprism surfaces from which the image replicas are emerging will provide similar results but at a lesser light throughput performance. FIG. 5A depicts another preferred embodiment said MBFO comprise a beam splitting element 500 disposed at a fixed location in the imaging path, defined as the space between the rear ending of said optical imaging optics means and their focal plane. Here, said TMF comprises a pair of ADSF-type multiband-pass filters 510, each disposed onto the tiltable axis of two tilting actuator means, interposed into the split ray paths, and said IHA comprises two MFA sensor arrangements for capturing the transmitted multiband filtered image replicas substantially simultaneously.

In one embodiment of present invention, said multi-bandpass filter means are disposed in front of said sensor array means and are tilted for tuning the transmitted spectral bands with the aid of said tilting actuator means 104. In another preferred embodiment of present invention, said tilting actuator means is mechanically coupled with a gearing mechanism (not shown) for transferring tilting motion to at least one said multi-bandpass filter means. In yet another embodiment of said MBFO, said tilting actuator means 104 effects the motion of only one said multi-bandpass filter. This embodiment may additionally include a second said sensor array capturing images transmitted or reflected by said beam splitter 500, without being filtered by said multiband pass filter means. The unfiltered image may comprise a reference image. The unfiltered image may also provide a substantially complementary set of said narrow band images by subtracting the images captured by said sensor array means filtered with said multi-bandpass filter means by said unfiltered image.

Figure 5B:
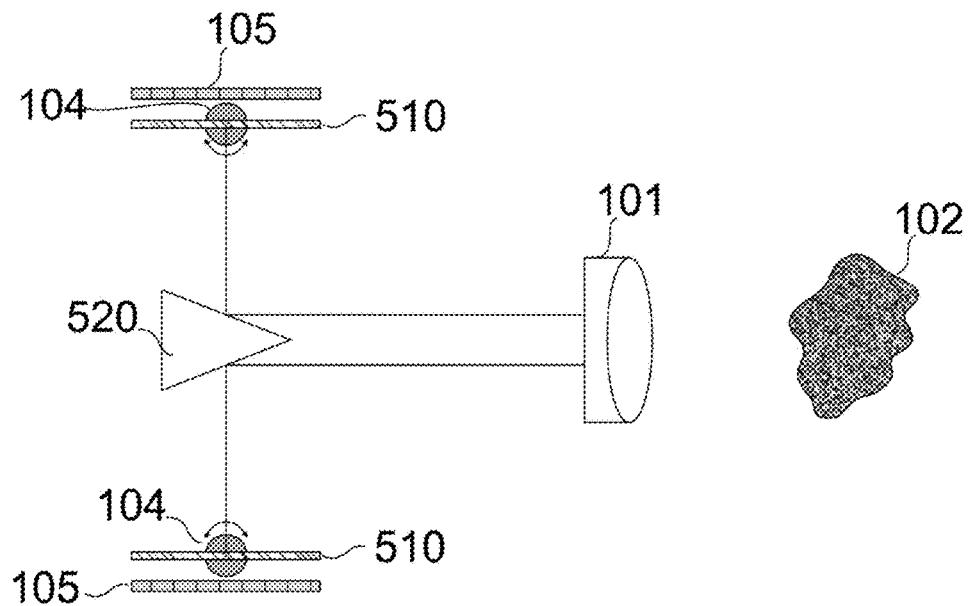

Reference now is made to FIG. 5B, which depicts yet another preferred embodiment of said MBFO of present invention, utilizing a prism 520 with its two sides being mirror coated. It is well understood to one skilled in the art that any kind of multisided reflectors including pyramid-type reflectors, tilting/rotating reflectors provide similar results with the concept of this embodiment. The mirrored sides divide the incoming beam into two identical branches and the filtering and image captured members are the same used in FIG. 5A.

Figure 5C:
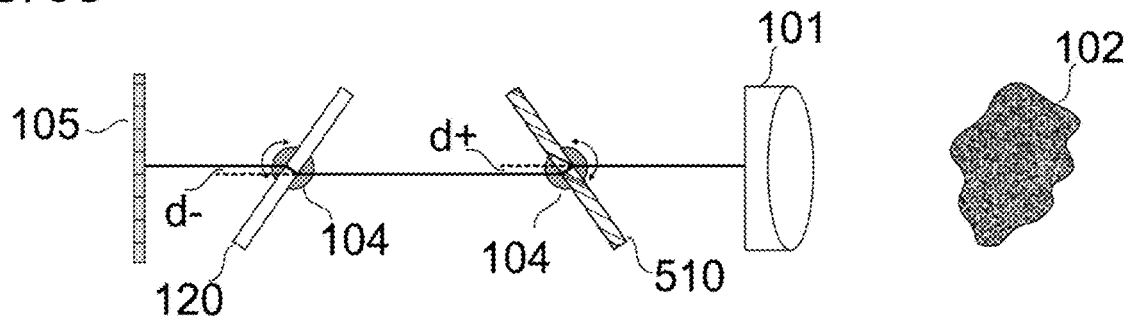

Reference now is made to FIG. 5C, which depicts optical arrangement means, compensating for shifting artifacts of the transmitted image, caused when tilting said plate polychroic mirror or said multi-bandpass filters.

Said transmitted image shift compensation eliminate the need for spatially translating said imaging array means, to follow said image shifting due to said MBFO tilting. Said image shifting compensation is achieved by inserting a glass plate 510 in the imaging ray path. Assuming that due to the thickness of said multi-bandpass filter, a d− displacement is provoked to the chief imaging ray, which is proportional to the tilting angle θ− (negative angles). According to present invention, said image shifting is corrected by adding a second (coated or uncoated) optical element 510, which is tilted at an opposite angle θ+ with respect to said horizontal axis. Tilting at θ+ results in an opposite displacement by d+ compensating displacement caused by said first optical element. Tilting of said second optical element is realized by said tilting actuator means 104, either directly or through a gearing mechanism. The thickness and the index of refraction of said glass plate can be properly tailored so that d−=d+ when θ−=θ+ indicating that the images focused on said image sensor means 105 are not shifted during spectral scanning.

Reference now is made to FIG. 6, which discloses additional embodiments of said IHA wherein said sensor array means is a single MFA imaging sensor onto which said MBFO arrangements generate tiled filtered image replicas. These embodiments are suitable for operation at fixed CSB, for instance when said hybrid spectral imager is intended for routine use in a filed with known spectral features. However, it is understood to one skilled in the art that spectral tunability can also be implemented to this case.

Figure 6A:
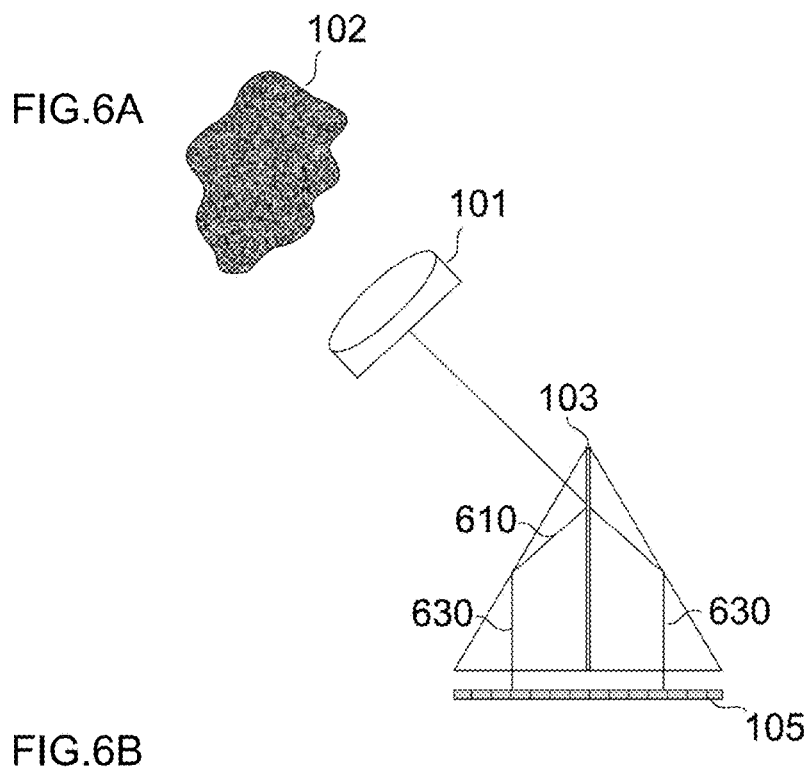
FIGS. 6A-6C show further embodiments of the present disclosure, where

FIG. 6A illustrates said MBFO comprising a modified Köster prism, which is disposed substantially over the active area of said MFA-imaging sensor. Said Köster prism 610 is typically made of two identical prisms (90°-60°-30°) cemented together along their longer vertical faces. The modification that it is claimed in present invention refers to the addition of a polychroic mirror coating 103, which is deposited onto one of said long vertical axis before cementing them together. Said Köster prism divides the incident beam 620 into two parallel and filtered beams 630, which are forming two identical, from the spatial information perspective, images. Said filtered images are focused side-by-side onto the surface of said single sensor 105. The distance between said two parallel beams 630 can be adjusted by varying the height of said incident beam 620. The path length of these two beams is substantially equal, which is essential for ensuring image focusing in both imaging paths. This way the described configuration can be adapted to a variety of sizes of said sensor array means.

Figure 6B:
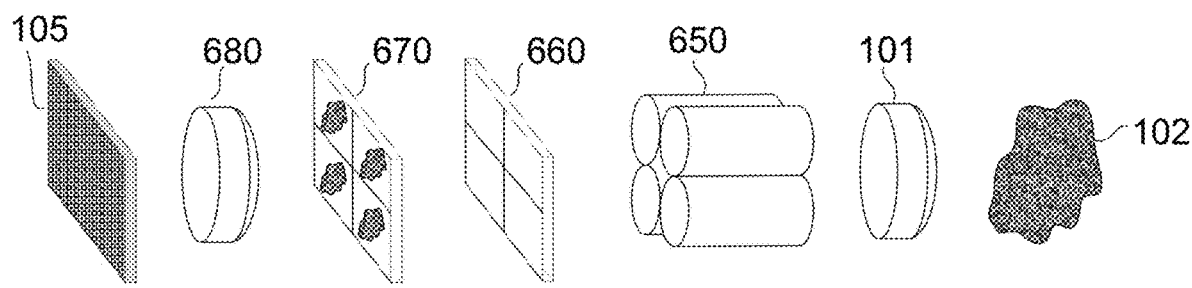

FIG. 6B depicts yet another embodiment of the present invention according to which a microlens array 650 refocuses the image formed at the focal plane of said objective lens optics 101, forming a set of identical images (image multiplication) onto a glass screen 670 after passing through a multiband pass filter array 660. Each filter, member of said filter array 660 filters the secondary image formed by the corresponding microlens, member of said microlens array 650. A relay lens 680 focuses the image displayed on said glass screen 670 onto said MFA imaging sensor 105. In another embodiment of present embodiment, said microlens array 500 is replaced with a multi-image prism (not shown), specially constructed to split the primary image to a number of said primary image replicas equaling with the number of the faces of said multi-image prism. In one variation of this embodiment, the faces of said multi-image prism are coated with different multiband pass filters, replacing, this way, said filter array 660. In yet another variation of embodiment depicted in FIG. 6 B, the elements 101, 650 (or any similar image multiplication optical arrangement), 660, 670 and 680 are housed together to comprise a stand-alone device, ending to a mount such as the one used in universal lenses. Said stand-alone device comprises an attachment that can be coupled to commercial cameras, converting them to a snapshot spectral imager. In yet another variation of said snapshot attachment, said relay lens 680 may be the embedded lens of a computing device e.g. mobile phone, tablet, camera. In that case said stand-alone snapshot module comprise a detachable accessory of said mobile phone and computer platforms.

Figure 6C:
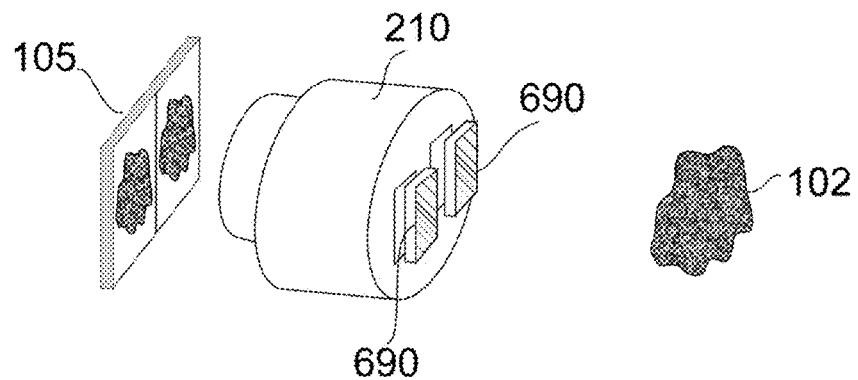

Reference now is made to FIG. 6C, which depicts yet another preferred embodiment, wherein said MBFO comprises a dual (or more) channel objective lens optics 210, with each channel being filtered by two said complementary multi-bandpass filters 690. Said filtered dual channel objective lens optics 210 have the property of focusing two spatially identical images, side-by-side, onto said MFA imaging sensor 105. According to the present invention, said dual channel objective lens optics are also considered the encapsulated to said mobile phone and computer platform dual lens/camera arrangements. In all these cases, said multi-bandpass filter means 510 are disposed at any point along the image focusing path.

In the next paragraphs, computational methods for achieving spectral purification of the imaging channels are disclosed. Due to the broadband nature of the primary color filters employed in said MFA, their transmission "tails" expand into the neighboring narrow transmission bands of said MBFO "contaminating" the spectral content of the recorded images.

Figure 7:
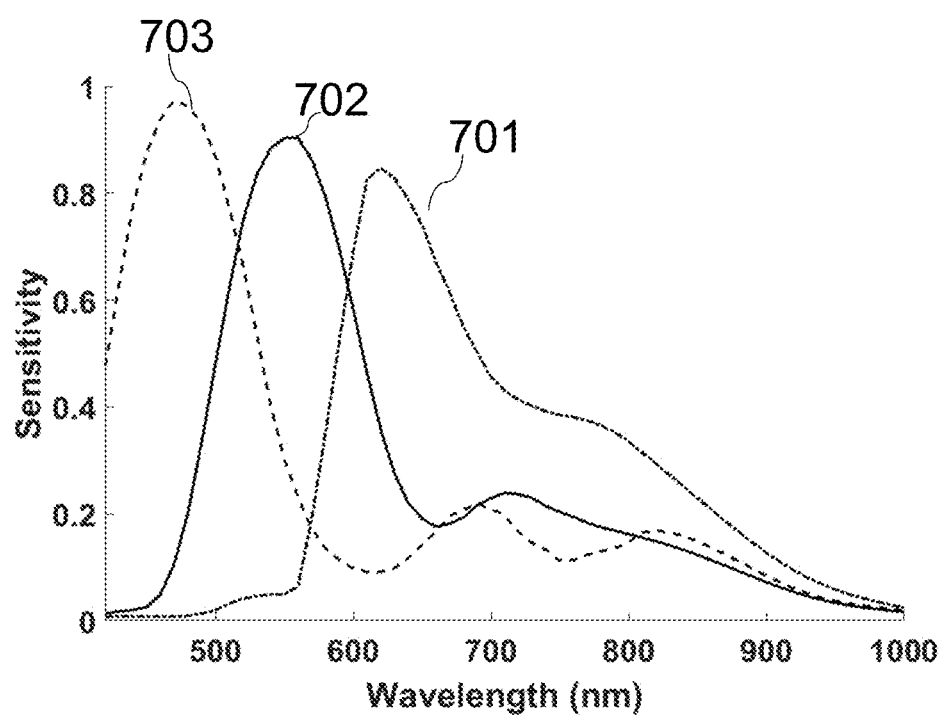
FIG. 7 depicts the primary color spectral responses of the Red (R), 701, Green (G) 702 and Blue (B) 703.

According to present invention, MFA-masked imaging sensor means are employed for recording multiple narrow-band images per image sensor. This option is adopted because a single said MFA-masked imaging sensor array can capture (after said spectral purification) at least three narrow band images, depending on the primary color/spectral filters used in the mosaic assembly. Three, four or more broadband filters make up commonly used MFA-imaging sensor arrays. FIG. 7 depicts an example of the spectral responses of the Red (R), 701, Green (G) 702 and Blue (B) 703 primary color channels, obtained from the specification's manual of a commercial MFA imaging sensor. As it can be seen, responses extend beyond upper limit of the visible spectrum (740 nm), going into the Near Infrared (NIR). Color cameras use a NIR rejection filter for the purpose of emulating human vison. For the same purpose, there is a significant spectral overlapping between said primary color channels.

Figure 8A:
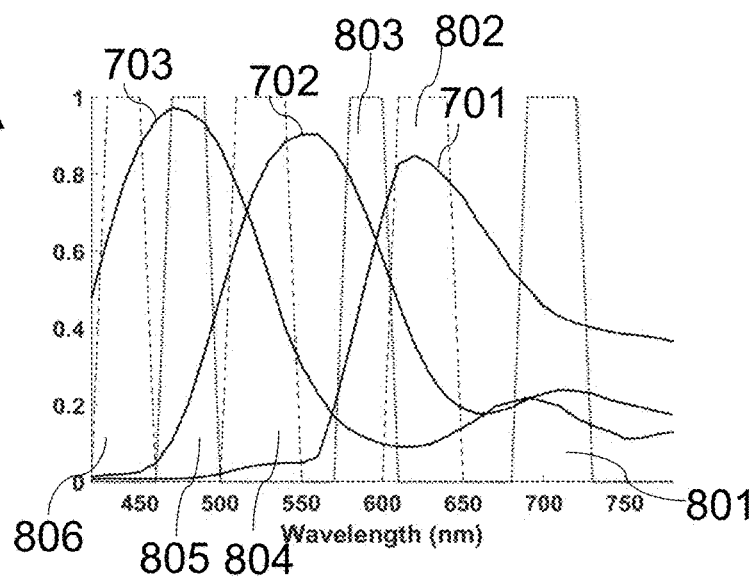
FIGS. 8A-8C depict one preferred embodiment for spectral imaging in the visible part of the spectrum where two MFA-FPA sensors and one six-band MBFO are used, where

FIG. 8A depicts the combined responses of said MBFO and said MFA from an IHA comprising two MFA imaging sensors, each comprising three filters, and a six-band MBFO. At is can be seen said combined responses are restricted to a set of six narrow spectral bands 801, 802, 803, 804, 805, and 806. This way, a first MFA sensor will capture the bands 801, 803, 805 and the second sensor will capture the bands 802, 804, 806. However, as it can be seen in FIG. 8B, the band 802 (for example) will be sampled predominantly by said R channel 701 of a second sensor. However, a certain amount of light energy 809 corresponding to this band will be captured by the G channel 702 and another amount 810 will be captured by the B channel. So together with the dominant bands, the broad MFA channels capture out of band contributions due to the spectral cross-talking.

The present invention discloses an experimental method for removing secondary contributions, originating from the spectrally overlapping responses of said MFA. This will allow for the restoration of said MBFO-bands.

According to the previous analysis, we can call the primary responses of MFA-channels as RR, GG, BB for Red, Green and Blue MFA channels accordingly. We can also call the secondary, out of band responses of the MFA-R channel as Rg (to Green) and Rb (to Blue). Accordingly, we have Gr (to Red) and Gb (to Blue) and Br (to Red) and Bg (to Green). We can then write MFA responses as follows:

$$R=RR+Rg+Rb, \quad (1),$$

$$G=Gr+GG+Gb, \quad (2),$$

$$B=Br+Bg+BB, \quad (3),$$

Restoring said MBFO-bands is equivalent to calculating RR, GG, BB from eqs 1, 2, 3, which requires the knowledge of said cross channel secondary contributions. However, for noise suppression purposes it is preferable to use the ratios between secondary and primary contributions, which are expressed as follows:

$$Crg=Rg/GG, \; Crb=Rb/BB$$

$$Cgr=Gr/RR, \; Cgb=Gb/BB$$

$$Cbr=Br/RR, \; Cbg=Bg/GG$$

By substituting said ratios, equations 1, 2, 3 become:

$$R=RR+Crg*GG+Crb*BB \quad (3),$$

$$G=Cgr*RR+GG+Cgb*BB \quad (4),$$

$$B=Cbr*RR+Cbg*GG+BB \quad (5),$$

which in matrix form and solved for MBFO-bands takes the form:

$$\begin{bmatrix} RR \\ GG \\ BB \end{bmatrix} = \begin{bmatrix} 1 & Crg & Crb \\ Cgr & 1 & Cgb \\ Cbr & Cbg & 1 \end{bmatrix}^{-1} * \begin{bmatrix} R \\ G \\ B \end{bmatrix} \quad (5)$$

Figure 8B:
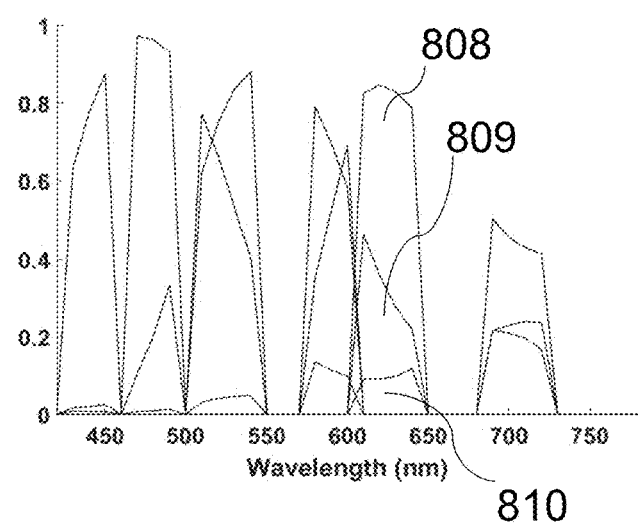

The 3×3 matric elements are measured as follows. A halogen light source coupled with a grating tunable monochromator was developed with the feature of enabling the control of the exited light power as a function of the selected wavelength. Said light source illuminate a calibration target with unity reflectance across the entire sensitivity range or said sensor array means (barium sulfide). A black and white sensor array is focused onto said calibration target and the tunable light source scans the spectrum. With feedback the responses recorded by said black and white sensor, the output power of said tunable light source is regulated so that said black and white sensor responses are flat across the entire spectrum. The setting of said tunable light source that compensate for the ramp-like responses of silicon sensors and halogen lamp are stored and are retrieved automatically when scanning is repeated. The next step is to replace said black and white sensor with said sensor array means with both MFA and MBFO and to repeat spectral scanning with the calibrated light source. The responses that are recorded are illustrated in FIG. 8B, where said primary and said secondary contributions are evident. From FIG. 8B and for a given said MFA and MBFO combination, said secondary/primary rations are found to be:

Crg=0.07, Crb=0.006, Cgr=0.435, Cgb=0.016, Cbr=0.133 and Cbg=0.73.

Figure 8C:
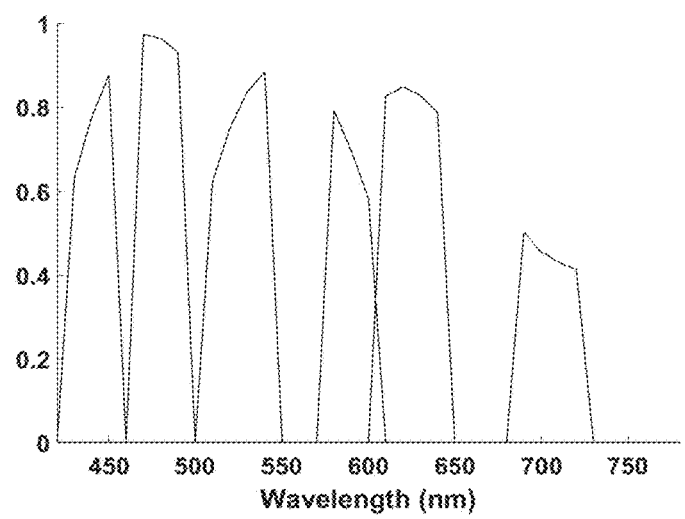

By substituting these values in matrix equation (5) the MBFO-bands are restored, free from out of band contributions as it is evidenced in FIG. 8C. By changing said tilting angle, the set of the six MBFO-bands will be shifted left or right depending on the sign of said tilting angle so that a full sampled spectral cube can be collected in the scanning mode of operation. The RGB primary color filters have a typical FWHM of about 150 nm. Therefore, each said primary color filter can record, for instance, fifteen (15) narrow band images of 10 nm FWHM each, totaling to about 45 non overlapping spectral images within the visible spectral range. This is a decent number ensuring sufficient spectral resolution and information-rich spectral cube.

Figure 9:
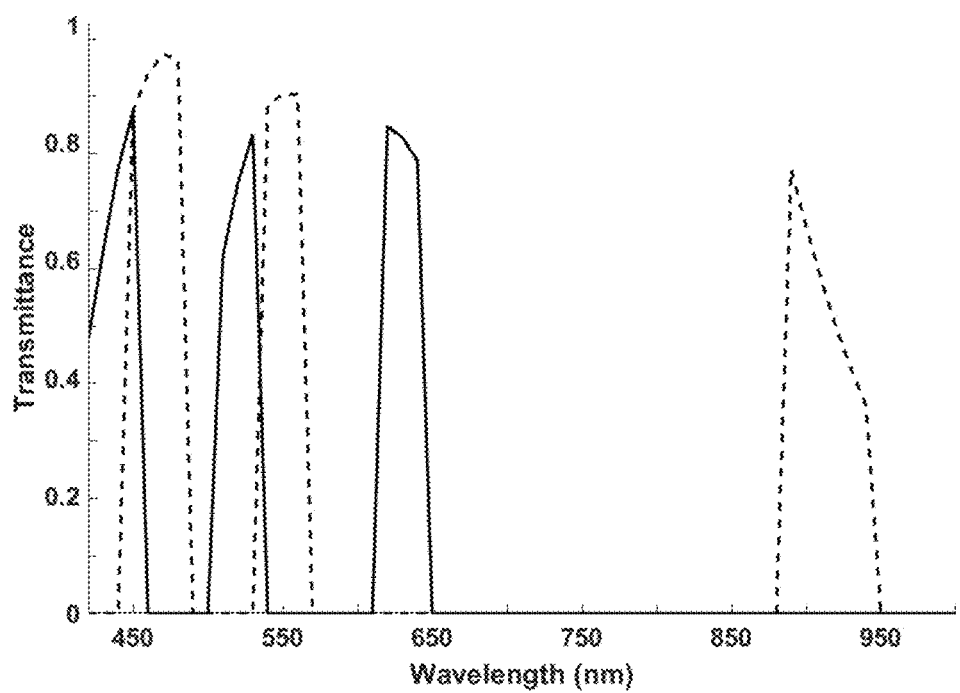
FIG. 9 illustrates another preferred embodiment for spectral imaging in both the visible and the near infrared part of the spectrum, wherein said MBFO arrangement, contains filtering optics means properly selected and disposed in the imaging ray path so that the first said MFA sensor to record 3 narrow band images in the visible part of the spectrum and the second said MFA sensor to record 2 narrow band images in the visible part of the spectrum and one narrow band image in the NIR (Near Infrared) part of the spectrum.

FIG. 9 illustrates an MBFO arrangement, which when it is combined with said MFA imaging sensor arrangement (with the NIR-cut filter removed), system's responses can be extended to NIR or to Ultraviolet spectral bands. On that basis, present invention claims embodiments implementing simultaneous real time imaging in the visible (color or spectral imaging) and non-visible spectral bands.

The descriptions below emphasize on methods for increasing spectral dimensionality through spectral estimation. Before proceeding with the relevant analysis, two key issues need to be clarified: a) in several applications of the disclosed hybrid spectral imager there will be no need for spectral estimation, since scanning mode operation will generate all necessary spectral information. The disclosed hyperspectral imager can ad hoc build or complement a similar to the test scene/sample training set, thus remarkably increasing spectral estimation accuracy; b) prior art systems use solely the broad MFA-RGB bands as a basis for spectral estimation, which is an unacceptable solution due to the ill-posed nature of this problem; c) prior art systems based on spectral estimation are limited in the visible part of the spectrum.

The present invention discloses a method improving estimation accuracy, when operating in the snapshot mode. By assuming a prior knowledge with regard to the nature, type or composition of an object or scene to be examined, a search can be conducted for identifying the spectral bands corresponding said prominent spectral features. Prior knowledge may refer to target scene-specific or object-specific spectral databases, meaning that have been generated for describing the spectral characteristics of specific targets or scenes in sufficient detail. Upon completing this task, the corresponding CSB are locked for performing snapshot spectral imaging. Due to sampling in the vicinity of prominent spectral features, the accuracy of the spectral estimation task is remarkably improved.

Figure 10A:
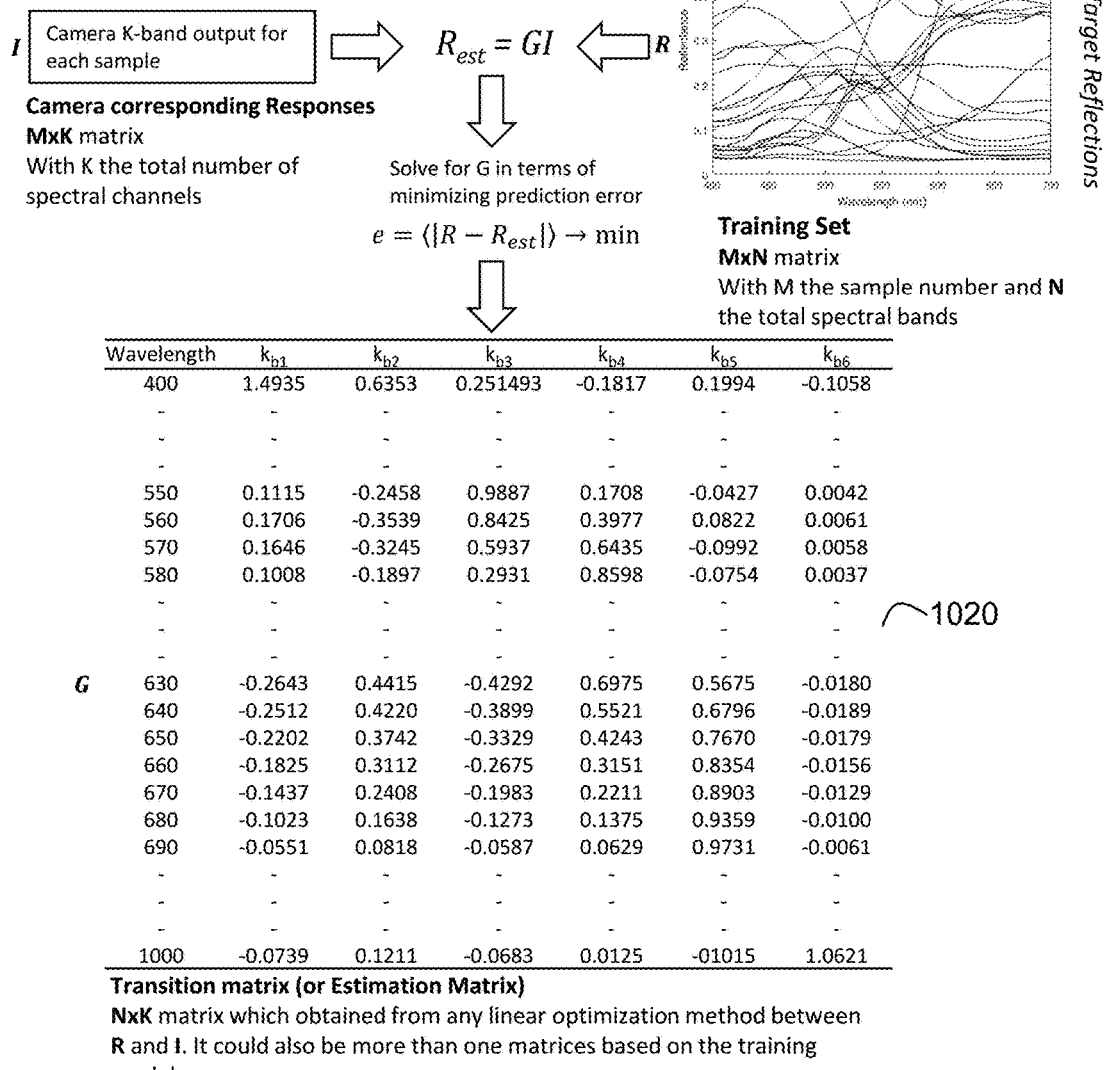
FIGS. 10A-10B illustrate a generic spectral estimation scheme utilizing said CSB as basis, where
Figure 10B:
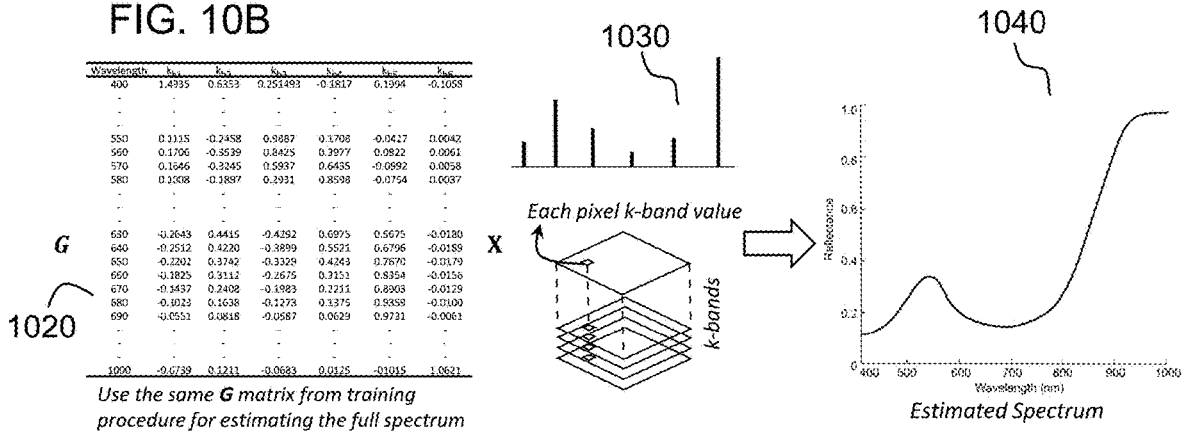

Reference now is made to FIG. 10, which illustrates a generic spectral estimation scheme utilizing said CSB as basis. FIG. 10 A depicts a training process involving a comparison attempting the best-match between the samples generated by a k-number CSB acquisition (test sample) and a training set comprising M spectra with N sampled data points (training set) 1010.

A spectral data base 1010, contain a sufficient number of spectra, which may be sampled in visible or in nonvisible spectral bands or combinations thereof. Additionally, the spectra may be labelled to represent a chemical identity, or a sample condition or a tissue pathology or combinations thereof. Several optimization methods can be employed for calculating the transition or estimation matrix 1020 including but not limited to Least Squares, Wiener Estimation, Kernel Methods, to Artificial Neural Networks and Sparse Reconstruction and Deep Learning approaches. As mentioned previously, several application-specific data bases can be developed for enabling complete-spectrum, snapshot spectral imaging in these fields. Said application-specific data bases 1010 and/or said estimation matrices 1020 may be pre-installed or downloadable to said mobile phone and computer platforms. FIG. 10 B illustrates schematically the spectral estimation after establishing said estimation matrix 1020, with the aid of which, the k-sparse data points 1030 are converted to a full spectrum 1040.

Another embodiment of the invention relates with the visualization of the huge spatial-spectral information that it is generated in real time with the disclosed hybrid spectral imager. The real time visualization of the spatial distribution of the various spectral classes contained in spectral cube is essential, especially in cases where these data comprise feedback for actions. In surgery, for example, areas with altered spectral profiles may comprise evidence for the present of an abnormality that need to be biopsied. In such cases, the real time display of a spectral class map is critical since the inspection probe (e.g. endoscope) or the tissue sample under inspection cannot be stable. The so-called spectral thematic maps may be displayed side-by-side with a color or spectral image and can be constructed in an unsupervised or supervised manner. The different classes present in a spectral cube can be visualized with the aid of artificial color-coding, with different classes being coded with different pseudocolors.

The spectra in a training data set may be labelled to represent, for example, a pathology status of a tissue, a chemical compound identity or a food quality condition. In that case, said spectral class mapper is converted to a pathology map for assisting, for example, in vivo or in vitro diagnosis, or to perform chemical or structural mapping for remote sensing and nondestructive analysis.

In yet another embodiment said hybrid spectral imager comprises a spectral photography camera, wherein instead of capturing photographs using the prior art three RGB primary color sensor, color reproduction in color photography is based on capturing the full spectrum across visible part of the spectrum. This embodiment has the implications in the color photography industry: a) color fidelity increases due to the expansion of color gamut; b) device and ambient light independent photography though the restoration of the object's spectral reflectance; c) metamerism-free photography.

In said spectral photography camera embodiment, said hybrid spectral imager uses the reflectance spectra obtained from the 1269 Munsell color chips as training set. Said Munsell data set is selecting as the most representative collection of spectra for color reproduction. A preliminary analysis is carried out on this data set for the purpose of determining the most populated by spectral features spectral bands.

Figure 11:
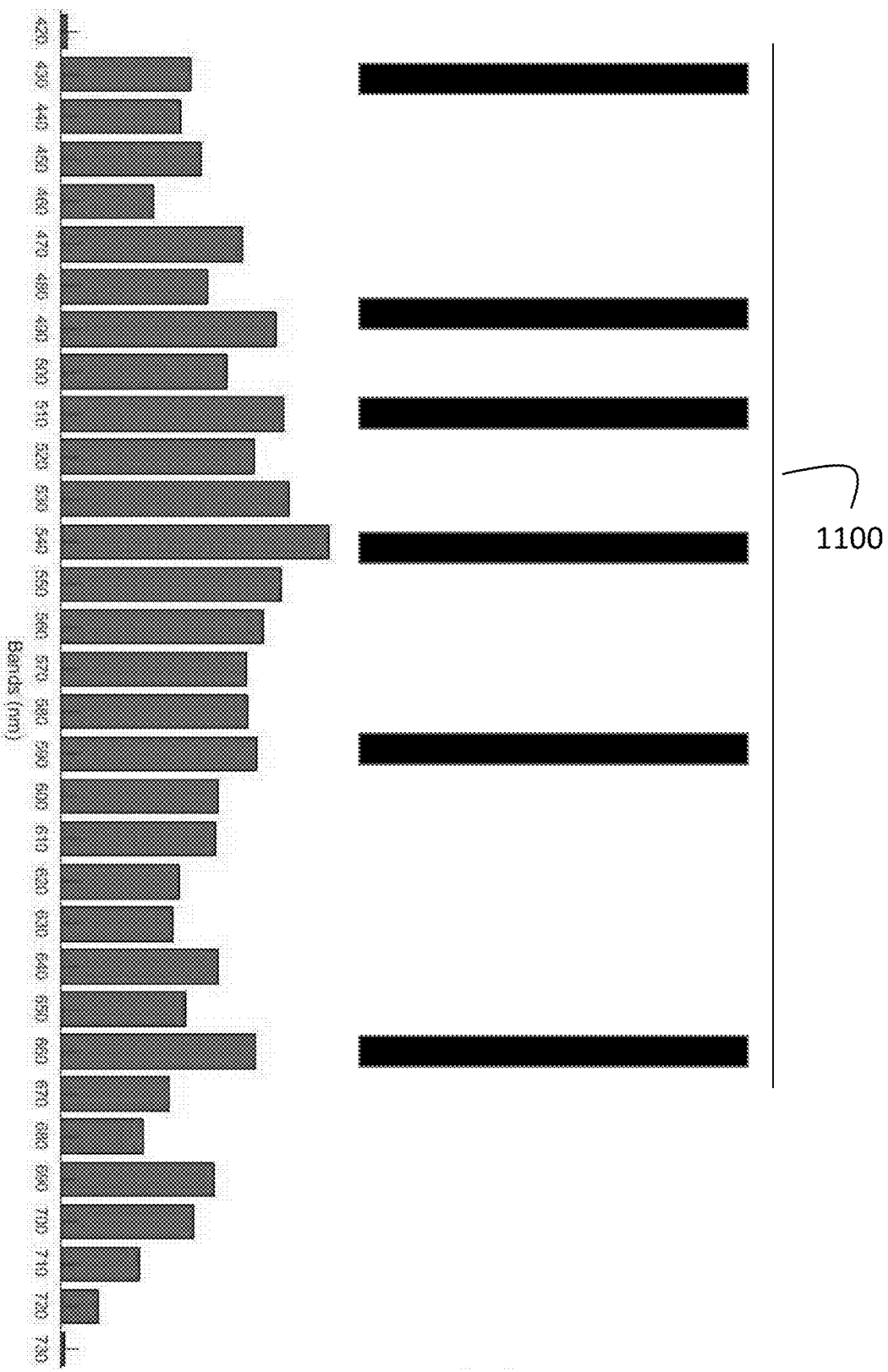
FIG. 11 illustrates the results of the analysis of a spectral data base, where the spectral are detected and shorted across the spectrum. The graph shows that said spectral features are widely spread and that there are spectral bands with higher population of said spectral features. These bands are good candidates to be selected as said CSBs.

FIG. 11 illustrates the results of this analysis showing that, as expected, the features are spread across the visible spectrum, however there are certain spectral bands with higher population 1100. These bands are adopted as said CSB for snapshot operation. It is obvious however to one skilled in the art that although inferior, similar results can be achieved by select CSB in the vicinity of the ones designated in FIG. 11. Upon capturing a CSB-image a full spectrum per pixel is estimated with spectral estimation using said Munsell 1269 spectra as a training set. Finally, the CIE tristimulus X, Y, Z color parameters are calculated for every pixel from the corresponding spectrum.

Figure 12:
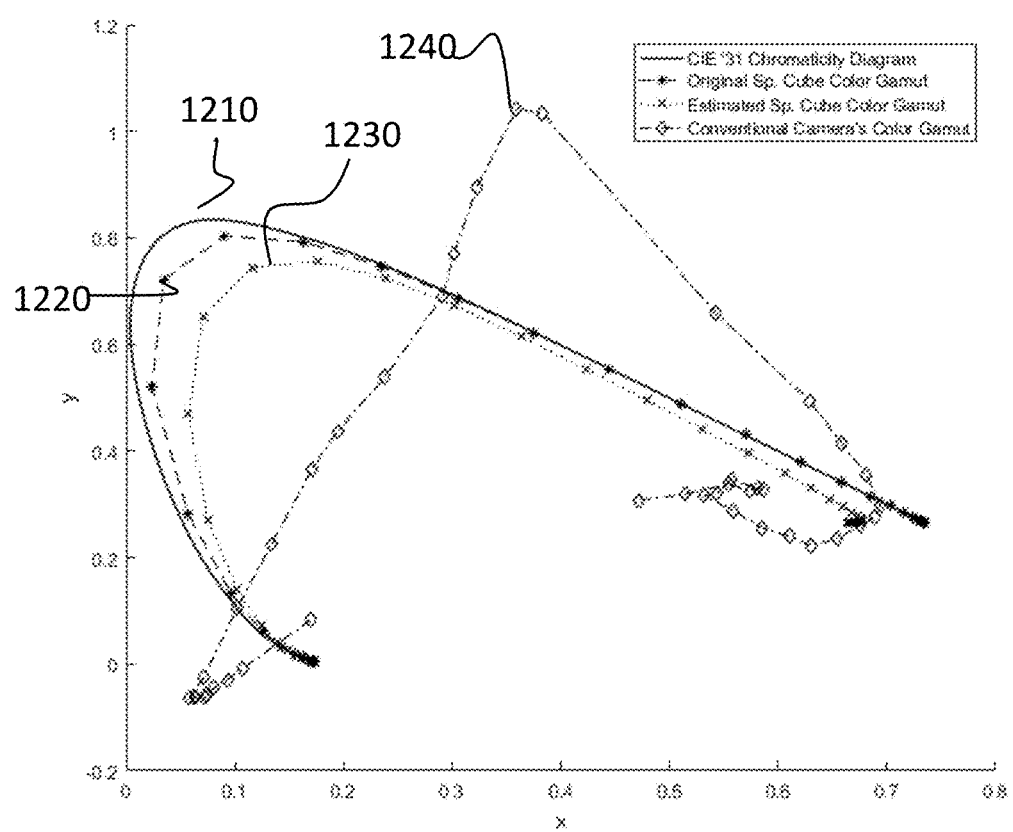
FIG. 12 illustrates the chromaticity diagram of a theoretical spectral locus compared with said locus produced with 3-color and hyperspectral cameras. Color gamut expansion achieved with current disclosure in clearly seen.

As it is evidenced in FIG. 12, digital spectral photography, which is implemented with the present embodiment improves notably the fidelity of color reproduction. The illustrated yx chromaticity diagram is derived from said X, Y, Z values and it comprises a standard method for quantifying color reproduction accuracy (fidelity) in the detection and reproduction industries. The external chromaticity locus (solid line) 1210 corresponds to the color response of the human eye. All the internal to this locus points correspond to the xy colors that can be reproduced by the human eye. A conventional RGB camera has a distant with the human eye color gamut 1240, for a significant area of the chromaticity locus. This indicates that there is a poor color reproduction fidelity for the corresponding colors. The best match with the human eye chromaticity locus is achieved with sampled-scanning hyperspectral imaging 1220, however scanning procedures cannot be acceptable for consumer photography. The snapshot/spectral estimation 1230 offers a color fidelity similar to the one achieved with scanning hyperspectral spectral imaging and, in any case, much superior to the fidelity achieved with the standard RGB cameras. Another distinct advantage of the claimed spectral photography apparatus over prior art RGB cameras is that they offer metamerism-free photography. In yet another embodiment of said spectral photography apparatus, standardized photography is achieved by estimating the spectral reflectance of the imaged object or scene. This may be realized thought the deconvolution of a) the illuminant's spectral power distribution; b) the spectral response of said sensor array means and c) said spectral reflectance. Once this is achieved, the component a) is replaced with the CIE's standard observer and component b) with the CIE's standard illuminant. The CIE's standard observer and illuminant functions are multiplied with said surface reflectance and their product is finally integrated over the wavelengths of the visible spectrum. The color photograph resulted from this process is perfectly standardized, since it is device and ambient light independent. As such, it can be used, for example, in telemedicine, in printing industry and in general in objective documentation. FIG. 8 and related description, provide a robust method for extracting said sensor's spectral responses. FIG. 9 discloses an MBFO arrangement providing extended sensitivity in the NIR part of the spectrum. Adopting this CSB configuration for said spectral photography apparatus, the infrared spectral band can be exploited for type of the illuminant used, since the most common illuminants have a distinct spectral profile in this spectral band. For instance, LED and fluoresce lamps have zero emission in the NIR, in contrary to what happens in the case of sun light and halogen lamps. Apart from that NIR sensitivity in said spectral photography apparatus would also enable haze-free photography.

The disclosed hybrid spectral imager integrates or is interfaced with a control and processing unit (CPU) integrating display means. The CPU and display means comprise at least in part, microcontroller units, memory units, FPGAs, mobile phones, tablet computers, lap top computers, flat displays and video googles. The CPU is coupled to the imaging head arrangement, executing program instructions for: a) calibrating image acquisition processes for compensating for the uneven response of said imaging sensor array means, across the spectrum and for the uneven spectral power distribution of the light sources illuminating said target scene object. Calibration is performed by utilizing imaging targets with unity (or known reflectance) reflectance across the operational spectral range, b) controlling and synchronizing the acquisition/capturing of the images by the MFA sensor arrangement at given tuning step of the TMF and for a plurality of said tuning steps; c) spectrally purifying the MFA sensor arrangement responses to compensate band cross-talking between the MFA and the TMF; d) processing spectral data for: training spectral estimation processes, estimating missing spectral data points and corresponding spectral images, classification and labeling of spectra, calculation and display of spectral thematic maps, chemical maps, pathology maps and combinations thereof.

Additional embodiments of the hybrid spectral imaging device, systems and methods according to the present invention are described below.

In one preferred embodiment, the disclosed IHA of FIGS. 4A-B, 5A-5C may operate with the MBFO member being locked to selected multiband filtering (MF) states, after establishing a knowledge with regard to the center wavelengths of the critical spectral bands (CSB) of an application filed. This knowledge may be established through a scanning operation of the disclosed hybrid spectral imager. In the locked MBFO state, the hybrid hyperspectral imager operates as a video rate spectral imager, reconstructing a complete hyperspectral cube through spectral estimation (FIG. 2). In another preferred embodiment the MBFO of the IHA (FIGS. 4A-B, 5A-5C) projects filtered images onto the sensor arrangement slightly displaced with each other to provide the necessary parallax so as to achieve spectral imaging and stereo imaging simultaneously.

The disclosed a video rate hyperspectral imager/mapper (VR-HIM) comprise a unique enabling solution in a long list of applications involving either dynamic phenomena or moving targets or applications requiring handheld operation with live spectral inspection capacity. In all these applications, the VR-HIM's MBFO first adapt to substantially match the CSB, which are, in principle, characteristic to the particular-applications specific detection/identification target(s). Next, the Central Processing Unit (CPU) executes program instructions with algorithms estimating the full hyperspectral cube content that includes estimated and acquired CSB data, and finally it calculates and displays at video rates a set of mapping images including color images, spectral images, spectral map images, spectral parameter images, chemical identity map images, pathology map images or growth status maps. Spectral map images are pseudocolored images with different artificial colors representing different spectral classes, defined with unsupervised classification algorithm means. Spectral parameter images are pseudocolored images with different artificial color representing parameter value ranges derived from spectra (e.g. peak-to-peak or peak-to-valley ratios, slopes, integrals etc). Pathology map images are pseudocolored images with different artificial colors representing spectral classes labelled with ground truth pathology data (e.g. biopsies, chemical analyses etc). Growth status map images are pseudocolored images with different artificial colors representing spectral classes labelled with ground truth growth identification data (e.g. presence of chemicals characteristic to ripening).

In another preferred embodiment of the VR-HIM intended to provide a crop imaging camera, the CSB correspond to the prominent spectral features such as peaks, and/or valleys, and/or slops of plant chromophores and fluorophores that are determining the phenotypes of the targeted plats, fruit, seeds etc. Chromophores, such as chlorophyll, and fluorophores are often affected by pathogens, fungal infections, water, salinity and nutrient stress factors that modify their macroscopic spectral patterns, thus comprising an assay for their detection. Visual inspection is often inadequate for probing early alterations, because of its limited spectral resolution and sensitivity range. Airborne and satellite hyperspectral platforms utilize scanning (push broom) techniques to collect spectra from crops in both the visible and the invisible spectral bands and calculate, from these spectra, vegetation index parameters, useful assessing e.g. the health status of plants. Although very useful, these crop inspection techniques are costly, they lack from flexibility and ease of use and are offering overview information not applicable, for example, to assessing fruit ripening. There is therefore an unmet need for real time, handheld hyperspectral imagers offering in-situ in the field spectral mapping of a long list of crop species including but not limited to plant leaves, stems, peduncles, fruits, flowers and seeds.

In another preferred embodiment, the present invention provides a crop hybrid spectral imager (CropHSI) with the MBFO tuned and locked to match the CSB of the crop species spectra in normal and altered conditions. The CPU of the CropHSI camera estimates the full hyperspectral cube content comprising both estimated and acquired CSB imaging data in real time and at full detector's spatial resolution. From the hyperspectral cube data, the control and processing unit (CPU) calculates and displays live color images side-by-side with spectral maps and/or pathology maps, when integrating training models and comparisons with ground truth data. Ground truth data are generated with plant models subjected, for example, to controlled stress conditions. Monitoring the change of the spectral profiles of the plant models, combined with sampling and destructive testing with reference methods establish the ground truth data, that are used the training of the CropHSI camera.

In yet another preferred embodiment, the CropHSI camera integrates a light source that match the sensitivity range of the IHA sensor arrangement. In still another preferred embodiment, the CropHSI camera integrates a dome-shaped light source, isolating ambient light and illuminating the examined object with diffusive light eliminating glare. The dome-shaped light source may include an array of narrow and broad band light sources. Narrow band light sources may include coherent and incoherent light sources for fluorescence excitation, when the CropHSI operates in the color and/or hyperspectral fluorescence imaging mode.

In one exemplary application, the CropHSI camera displays at video rates color images, spectral images and characteristic patterns of spectral maps and/or pathology maps facilitating the control and the optimization of farming by enabling reduced use of fertilizers, pesticides and water, through the regular monitoring of crop health status, in situ, in the field and non-destructively.

In another exemplary application, the CropHSI camera displays at video rates color images, spectral images and characteristic patterns of spectral maps and/or pathology maps facilitating the in situ, in-the-field and the non-destructive identification of conditions including pathogens, fungal infections, water, salinity and nutrient stress conditions.

In yet another exemplary application, the CropHSI camera displays at video rates color images, spectral images and characteristic patters of spectral maps and/or pathology maps facilitating fruit ripening assessment to predict the optimal harvest date.

In still another exemplary application, the CropHSI camera displays at video rates color images, spectral images and characteristic patters of spectral maps and/or chemical identity maps facilitating food quality assessment.

In another preferred embodiment of the VR-HIM intended to provide a marine imaging camera, the disclosed hybrid spectral imager may be configured to scan the visible and the NIR spectrum and to adapt and lock to CSB corresponding to maximum visibility through murky/turbid waters. The acquired and estimated imaging hyperspectral cube imaging data may be utilized to estimate and remove the scattering component that deteriorates image colors and contrast. It is known that both Rayleigh and Mie scattering cross-sections are inversely proportional with the wavelength and that water absorption increases with the wavelength. Moreover, the concentration of light absorbing and scattering suspensions may vary from point to point within the imaged water volume. When the hybrid spectral imager is configured to provide an underwater (UW) camera (UWHSI) the CSB include spectral bands in both the visible and the Near Infrared (NIR) part of the spectrum. NIR imaging is essential since it comprises a spectral zone, at which water has lower back scattering cross section, as compared to the visible band and slightly higher absorption coefficient. Spectral data captured in both the visible and the NIR bands may be used to extract the scattering component, for effecting image dehazing and color restoration in real time, thus offering an artificial vision tool for improving underwater visibility. Algorithms applied to the acquired and estimated spectral cube imaging data are selected from a group comprising at least in part fusion algorithms, and convolution neutral networks (CNN). The UWHSI may be mounted on a stationary stand or on a floating (surface of subsurface) platform (FP) and transfer, through e.g. a Gigabit Ethernet line, acquired and estimated spectral cube data offering multimodal inspection, with imaging modes selected from a Graphical User Interface (GUI) and comprising color images, spectral images, spectral maps, spectral parameter maps, and dehazed images to land/deck or underwater stations/displays.

In one exemplary application, the UWHSI camera is used for the underwater inspection and monitoring of fish activity, feeding status, welfare and waste.

In another exemplary application, the UWHSI camera is used for inspecting the ship's hull for assessing, for example, the status of biofouling deposits and for guiding cleaning operations. One way for obtaining biofouling mapping, while at the same time ensuring maximum visibility is to use the "red edge" vegetation index type spectral parameter mapping, calculated from the spectra in the range 680-780 nm.

In yet another exemplary application, the UWHSI camera is used for measuring the underwater visibility through the measurement of the scattering coefficient as a function of the wavelength or thought the measurement of the scattering-induced edge spreading as a function of the wavelength in natural or artificial targets.

In yet another preferred embodiment of the VR-HIM intended to provide a medical scope camera (MS-HSI), the optical imaging means for collecting and focusing an image of a target scene or object along an imaging path, is any medical scope used for in vivo clinical inspections, optically coupled with the IHA through a thread. Medical scopes may include, for example, the endoscopes, the clinical/surgical microscopes and the macro imaging scopes. As it is defined herein, the macro imaging scopes are scopes with typical field-of-view lying in the range of a few millimeters to few centimeters. The endoscopes comprise a medical scope subclass that include at least the laparoscopes, the laryngoscopes, the hysteroscopes, the cystoscopes (bladder), the nephroscopes (kidney), the bronchoscopes (bronchus), the arthroscopes (joints) and the gastrointestinal endoscopes. The medical scope subclass of clinical/surgical microscopes include at least the surgical microscopes, the colposcopes, the ophthalmic microscopes, and the Ear Nose and Throat (ENT) microscopes. The medical scope subclass of the macro imaging scopes includes but are not limited to dermoscopes, blood perfusion imagers, ophthalmoscopes and fundus cameras.

The MBFO of the MS-HSI is tuned to match the CSB of the spectra corresponding to either the intrinsic (native) or to the externally administered chromophores and fluorophores and specifically referring to the ones that are changing with tissue status and pathologies. The CPU of the MS-HSI camera estimates the full hyperspectral cube content comprising both estimated and acquired CSB imaging data in real time and at full detector's spatial resolution. From the hyperspectral cube data, the CPU calculates and displays the mapping images including live color images, spectral images, spectral maps and/or pathology maps. Pathology maps is the result of system's training based on the comparison between spectral profiles and biopsy/histology results, both obtained from the same tissue location. Spectral images may include UV, visible and NIR images, and spectral maps may refer to either reflectance or fluorescence spectral maps. In the former case, tissue illumination is provided from a broadband light source comprising coherent or incoherent solid state or black body light sources or combination thereof. In the case of operating in the fluorescence operation mode, tissue illumination is provided from the light source arrangement that includes coherent and incoherent narrow band excitation light sources with their emission center wavelengths being in the vicinity of the excitation maxima of targeted exogenous and endogenous fluorophores, that need also to spectrally overlap with the complementary to MBFO bands, so that light source is effectively blocked from the imaging path. For example, when the targeted fluorophore is the externally administered indocyanine green (ICG), a fluorophore that binds on plasma proteins, the excitation band is set within the 600-800 nm band and the emission band is selected within the 850-1000 nm band. Since fluorescence emission of ICG is found in the NIR, the disclosed invention allows for simultaneous live display of both reflectance and fluorescence spectral imaging. Other examples of externally administered contrast agents include 5-Aminolevulinic acid (ALA), acetic acid dilute solution, lugol iodine, methylene blue, molecular markers and quantum dots. MS-HSI camera may operates in a time-lapse hyperspectral imaging mode for monitoring the dynamic optical effects associated with the pharmacokinetics of contrast agent-tissue interaction, in several spectral bands simultaneously for a given time point. In that case, the mapping images may be obtained dynamically for a given time point and for a plurality of time points.

Mapping images and particularly pathology maps may be based on either the diffuse reflectance or the fluorescence imaging mode and may comprise an adjunctive tool to assist both the noninvasive diagnosis and to guide biopsy sampling and surgical excisions on a negative (for pathology) margins.

In one exemplary implementation of the MS-HSI to endoscopy, the endoscope is the endoscope used to examine the endometrium, known as hysteroscope. MS-HSI hysteroscope comprise the VR-HIM connected with an endoscopy light source. The light source is connected to the lighting port of the hysteroscope, emitting, on demand, broad-band and narrow-band light for enabling diffuse reflectance and reflectance imaging respectively. Both the VR-HIM and the endoscopy light source are controlled and synchronized by the CPU. The CSB of the MS-HSI hysteroscope include NIR spectral bands for visualizing subsurface features, essential for detecting endocervical dysphasia and cysts. The MS-HSI hysteroscope operates in two modes of operation, namely: the reflectance and the fluorescence mode, both acquiring imaging data either from native tissues or from or externally administered contrast agents interacting with the endometrial tissue and displays, substantially simultaneously and at video rates, mapping images that include spectral images, spectral map images and/or pathology images together with a color reference image. The mapping images may be used as an adjunctive assay to clinical diagnosis for a long list of endometrial pathologies, offering an objective means for follow up for minimizing the need for invasive biopsies and for guiding surgical treatments. The endometrial pathologies are selected from a group comprising polyp tissues, dysplastic tissues, cancerous tissues endometritis tissues, and atypical uterine bleeding (AUB) tissues. These conditions often comprise the grounds of infertility and therefore the mapping images offer a means for their early detection and for objectively monitoring the effectiveness of treatments, thus increasing the chances for pregnancy. It also offers a means for guiding the implantation of fertilized eggs at the right time widow and tissue area as a means for reducing multiple and ectopic pregnancies.

Another exemplary implementation of the MS-HSI is for clinical/surgical microscopy. The clinical/surgical microscope is the colposcope used to examine the cervix of the uterus. The MS-HSI colposcope comprises the VR-HIM connected with light spot projector, illuminating the field-of-view of the VR-HIM. The light source emits, on demand, broad-band and narrow-band light for enabling diffuse reflectance and reflectance imaging respectively. Both the VR-HIM and the spotlight source are controlled and synchronized by the CPU. The CSB of the MS-HSI colposcope include ultraviolet reflection bands for enhancing the visualization of the transformation zone between squamous and columnar epithelium, which very often comprise the location of high-grade cervical neoplasia. CSB further include visible bands for visualizing the acetowhitening kinetics and NIR bands that are used for normalizing the acetowhitening and lugol iodine diagnostics uptake in the visible bands and for discriminating leukoplasias from acetowhitened epithelium. The MS-HSI colposcope operates in two modes of operation, namely: the reflectance and the fluorescence mode, both acquiring imaging data either from native tissues or from or externally administered contrast agents interacting with the endometrial tissue and displays, substantially simultaneously and at video rates, mapping images that include spectral images, spectral map images and/or pathology images together with a color reference image. The mapping images may be used as an adjunctive assay to clinical diagnosis for a long list of cervical pathologies, offering an objective means for follow up for minimizing the need for invasive biopsies and for guiding surgical treatments. The cervical pathologies are selected from a group comprising Cervical Intraepithelial Neoplasia (CIN), Human Papilloma Virus (HPV), cancer, leukoplakia, and inflammation. When the MS-HIS colposcope operates in the time-lapse imaging for monitoring the dynamic optical effects associated with the pharmacokinetics of acetic acid solution-tissue interaction, it includes the 90 s time point after the application of the agent, since it has been found that it is informative for discriminating low from high grade CIN.

In yet another exemplary implementation, the MS-HSI hysteroscope and the MS-HSI colposcope are both integrated in a single workstation sharing at least the CPU and the display means In yet another exemplary implementation of the MS-HSI macro imaging scopes, the macro imaging scope is a dermoscope used to examine skin pathologies including hair and nail pathologies. MS-HSI dermoscope comprise the VR-HIM coupled with a dome light source. The disclosed dome-based dermoscope offers the distinct advantage of illuminating the skin tissue indirectly and after the light rays being subjected to multiple reflections onto the domes diffusive walls. Dome illumination eliminates glare, provides diffusive light, essential for measurement and analysis of diffuse reflectance spectra, which are critical for spectroscopy-based diagnosis of skin malignancies. The dome module encapsulates a light source array emitting, on demand, broad-band and narrow-band light for enabling diffuse reflectance and reflectance imaging respectively. Both the VR-HIM and the dome light source are controlled and synchronized by the CPU. The CSB of the MS-HSI dermoscope include the peaks, valleys and slopes of skin hair and nail chromophores spectra e.g. oxy-hemoglobin, deoxy-hemoglobin, pheomelanin and eumelanin, bilirubin, which span the spectral band 360-1100 nm. CSB include also the peaks, valleys and slopes of contrast agents and skin native fluorophores. This invention discloses that the spectral classification in the spectral band 650-1100 nm discriminates between dysplastic, melanoma and benign nevi and especially the finding that the absorption coefficient of these moles increases with their histological grade. The MS-HSI dermoscope operates in two modes of operation, namely: the reflectance and the fluorescence mode, both acquiring imaging data either from native tissues or from or externally administered contrast agents interacting with skin tissue and displays, substantially simultaneously and at video rates, mapping images that include spectral images, spectral map images and/or pathology images together with a color reference image. The mapping images may be used as an adjunctive assay to clinical diagnosis for a long list of skin pathologies, offering an objective means for follow up, for minimizing the need for invasive biopsies and for guiding surgical treatments. The skin pathologies are selected from a group comprising melanocytic and non-melanocytic cancers and precancers, fungal infections, sebum excretion analysis, acne and hormone disorders, systematic sclerosis conditions, erythema and irritation present in dermatitis, allergic reactions, photosensitivity and blood perfusion disorders e.g. due to diabetes.

The examples used above to describe the present innovative solution should not be viewed as limiting the scope of the present innovative solution. The present innovative solution may be applied to use scenarios and settings other than those described in the presented examples.

The above exemplary are intended for use either as a standalone system or method in any conceivable scientific domain, or as part of other scientific methods, processes and systems.

Various embodiments of the invention are described above in the Detailed Description. While these descriptions directly describe the above embodiments, it is understood that those skilled in the art may conceive modifications and/or variations to the specific embodiments shown and described herein unless specifically excluded. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

In one or more exemplary embodiments, the functions described may be implemented in hardware, software, firmware, or any combination thereof. If implemented in software, the functions may be stored on or transmitted over as one or more instructions or code on a computer readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer or any other device or apparatus operating as a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A hybrid spectral imager apparatus comprising:
   an imaging head arrangement (IHA) comprising:
      optical imaging means for collecting and focusing an image of a target scene or object along an imaging path;
      multiband filtering optics (MBFO) means comprising:
         beam divider means for generating at least two replica images of the target image; and
         multiband filtering (MF) means interposed into the imaging path and effecting multi-bandpass filtering in the images replicas; and
   a sensor arrangement comprising at least one Mosaic filter array (MFA) focal plane array (FPA) sensor onto which the multiband filtered image replicas are focused, comprising focal plane array means masked, in a pixelized manner, with at least three wide-band primary color-type filters, with each primary color-type response separating and capturing one single-band image component from the multiband-filtered image replicas;
   a control and processing unit (CPU) coupled to the IHA and configured to execute program instructions for: calibrating image acquisition processes; controlling and synchronizing the acquisition/capturing of the image replicas by the MFA sensor arrangement; and spectrally purifying the MFA sensor arrangement responses to compensate band cross-talking between the MFA and the MF; and
   display means for displaying on a user interface means at least the acquired single-band images;
   wherein the CPU is configured to reconstruct and display, on the display means, a set of at least three different single-band images per MFA-FPA sensor employed; and
   wherein the IHA is configured to capture sets of different single-band images for video snapshot spectral imaging at desired spectral bands within the FPA sensor arrangement spectral sensitivity range.

2. The hybrid spectral imager apparatus of claim 1, wherein the MF comprises a tunable multiband filtering (TMF) arrangement.

3. The hybrid spectral imager apparatus of claim 1, further comprising a video rate hyperspectral imager/mapper (YR-HIM) operational mode, wherein the MBFO is set to substantially match the center wavelengths of Critical Spectral Bands (CSB), characteristic to an identification target, wherein the estimated full hyperspectral cube content is calculated with spectral estimation and includes estimated and acquired CSB data, and wherein the mapping images include color, spectral, chemical identity or pathology maps are calculated and displayed at video rates from the estimated full hyperspectral cube.

4. The hybrid spectral imager apparatus of claim 3, wherein the YR-HIM is a crop imaging camera, the CSB characteristic to an identification target are CSB of the crop species spectra in normal and altered conditions, and wherein the mapping images are selected from a group comprising color images, spectral images, spectral map images, spectral parameter images.

5. The hybrid spectral imager apparatus of claim 4, further comprising means for labeling through training the spectral classes with ground truth data.

6. The hybrid spectral imager apparatus of claim 5, wherein the mapping images are selected from a group comprising color images, spectral images, spectral map images, spectral parameter images, chemical identity map images and pathology map images, and wherein the targeted identification of conditions are selected from a group comprising at least in part pathogens, fungal infections, water, salinity and nutrient stress conditions.

7. The hybrid spectral imager apparatus of claim 3, wherein the VR-HIM is a fruit ripening imaging camera, the CSB characteristic to an identification target are CSB of fruits/produces at different growth states, and wherein the mapping images are selected from a group comprising color images, spectral images, spectral map images, spectral parameter images, chemical identity map images, pathology map images or growth status maps.

8. The hybrid spectral imager apparatus of claim 3, wherein the YR-HIM is a food quality imaging camera, the CSB characteristic to an identification target are CSB of food items in different quality levels, and wherein the mapping images are selected from a group comprising color images, spectral images, spectral map images, spectral parameter images, chemical identity map images, pathology map images or growth status maps.

9. The hybrid spectral imager apparatus of claim 3, wherein the YR-HIM is an underwater imaging camera, the CBS include spectral bands in both the visible and the Near Infrared part of the spectrum, and wherein the mapping images comprise imaging modes selected from a Graphical User Interface (GUI) menu and comprising color images, spectral images, spectral maps, spectral parameter maps, and dehazed images inspected in land/deck or underwater stations/displays.

10. The hybrid spectral imager of claim 9, wherein the UWHSI camera is used for the underwater inspection and monitoring of fish activity, feeding status, welfare and waste.

11. The hybrid spectral imager of claim 9, wherein the UWHSI camera is used for inspecting the ship's hull for assessing the status of biofouling deposits and for guiding cleaning operations, and wherein the red edge spectral mapping is used as a means for quantifying the biofouling status.

12. The hybrid spectral imager of claim 9, wherein the UWHSI camera is used for measuring the underwater visibility with the measurement of the scattering coefficient as a function of the wavelength or with the measurement of the scattering-induced edge spreading in natural or artificial targets as a function of the wavelength or with combinations thereof.

13. The hybrid spectral imager of claim 1, wherein optical imaging means for collecting and focusing an image of a target scene or object along an imaging path are selected from a group comprising endoscopes, clinical surgical microscopes, dermoscopes and ophthalmoscopes.

14. The hybrid spectral imager of claim 3, wherein optical imaging means for collecting and focusing an image of a target scene or object along an imaging path are selected from a group comprising endoscopes, clinical surgical microscopes, dermoscopes and ophthalmoscopes.

15. The hybrid spectral imager apparatus of claim 3, wherein the YR-HIM is a medical scope camera (MS-HSI), the CSB characteristic to an identification target are CSB of the intrinsic (native) or to the externally administered chromophores and fluorophores known that are changing with tissue status and pathologies, and wherein the mapping images diffuse reflectance or fluorescence color images, spectral images, spectral maps and/or pathology maps.

16. The hybrid spectral imager apparatus of claim 14, wherein externally administrated contrast agents include 5-Aminolevulinic acid (ALA), acetic acid dilute solution, lugol iodine, methylene blue, molecular markers and quantum dots.

17. The hybrid spectral imager apparatus of claim 14, wherein the MS-HSI is programmed to operate in a time-lapse hyperspectral imaging mode for monitoring the dynamic optical effects associated with the pharmacokinetics of contrast agent-tissue interaction, in several spectral bands simultaneously for a given time point and wherein the mapping images are obtained dynamically for a given time point and for a plurality of time points.

18. The hybrid spectral imager apparatus of claim 14, wherein the optical imaging means is a hysteroscope for examining endometrial tissue, wherein the CSB include NIR spectral bands and wherein the mapping images are used as an adjunctive assay to clinical diagnosis of endometrial pathologies selected from a group comprising polyp tissues, dysplastic tissues, cancerous tissues endometritis tissues, and atypical uterine bleeding (AUB) tissues and as a guide for implantation of fertilized eggs at the right time widow and tissue area as a means for reducing multiple and ectopic pregnancies.

19. The hybrid spectral imager apparatus of claim 14, wherein the optical imaging means is a colposcope for examining the cervix of the uterus, wherein the CSB include ultraviolet reflection bands for visualizing the transformation zone, visible bands for visualizing the acetowhitening kinetics and NIR bands for normalizing that are used for normalizing the acetowhitening and lugol iodine diagnostics uptake in the visible bands and for discriminating leukoplasias from acetowhitened epithelium and wherein the mapping images refer to both native and externally administrated fluorophores and chromophores in static and time lapse modes mapping images, which are used as an adjunctive assay in the clinical diagnosis of cervical tissue pathologies selected from a group comprising Cervical Intraepithelial Neoplasia (CIN), Human Papilloma Virus (HPV), cancer, leukoplakia, and inflammation.

20. The hybrid spectral imager apparatus of claim 14, wherein the MS-HSI hysteroscope and the MS-HSI colposcope are both integrated in a single workstation sharing at least the CPU and the display means.

21. The hybrid spectral imager apparatus of claim 14, wherein the optical imaging means is a is a macro imaging lens means for the skin and its hair and nail accessories, wherein the CSB include the wavelengths of peaks, valleys and slopes of the spectra of skin, hair and nail native or externally administrated chromophores and fluorophores such as oxy-hemoglobin, deoxy-hemoglobin, pheomelanin and eumelanin, bilirubin, spanning the spectral band 360-1100 nm, and wherein the mapping images are used as an adjunctive assay to clinical diagnosis of skin pathologies are selected from a group comprising melanocytic and non-melanocytic cancers and precancers, fungal infections, sebum excretion analysis, acne and hormone disorders, systematic sclerosis conditions, erythema and irritation present in dermatitis, allergic reactions, photosensitivity and blood perfusion disorders e.g. due to diabetes.

22. The hybrid spectral imager apparatus of claim 14, wherein the diffuse reflectance absorption coefficient spectrum of skin moles/nevi in the spectral range 650-1100 nm is used as an assay for discriminating between dysplastic, melanoma and benign nevi.

23. The hybrid spectral imager of claim 1, further comprising a dome light source encapsulating a light source array emitting, on demand, broad-band and narrow-band light for diffuse reflectance and reflectance imaging respectively, illuminating the examined objects indirectly and after the light rays being subjected to multiple reflections onto the dome's diffusive walls.

24. The hybrid spectral imager of claim 4, further comprising a dome light source encapsulating a light source array emitting, on demand, broad-band and narrow-band light for diffuse reflectance and reflectance imaging respectively, illuminating the examined objects indirectly and after the light rays being subjected to multiple reflections onto the dome's diffusive walls.

25. The hybrid spectral imager of claim 20, further comprising a dome light source encapsulating a light source array emitting, on demand, broad-band and narrow-band light for diffuse reflectance and reflectance imaging respectively, illuminating the examined objects indirectly and after the light rays being subjected to multiple reflections onto the dome's diffusive walls.

26. The hybrid spectral imager of claim 1 wherein the MBFO of the IHA projects filtered images onto the sensor arrangement, slightly displaced with each other to provide the necessary parallax for acquiring and displaying spectral imaging and stereo imaging simultaneously.

\* \* \* \* \*